(12) United States Patent
Birnkrant et al.

(10) Patent No.: US 10,814,082 B2
(45) Date of Patent: Oct. 27, 2020

(54) COMBINATION RESPIRATORY THERAPY DEVICE, SYSTEM AND METHOD

(71) Applicant: MHS Care-Innovation, LLC, Cleveland, OH (US)

(72) Inventors: David J. Birnkrant, Moreland Hills, OH (US); Chad M. Boerst, Blaine, MN (US); Michael Yang ChangGuo, Singapore (SG)

(73) Assignee: MHS CARE-INNOVATION, LLC, Cleveland, OH (US)

( * ) Notice: Subject to any disclaimer, the term of this patent is extended or adjusted under 35 U.S.C. 154(b) by 341 days.

(21) Appl. No.: 15/789,280

(22) Filed: Oct. 20, 2017

(65) Prior Publication Data
US 2018/0043116 A1    Feb. 15, 2018

Related U.S. Application Data

(63) Continuation of application No. 13/692,192, filed on Dec. 3, 2012, now Pat. No. 9,795,752.

(51) Int. Cl.
*A61M 16/00* (2006.01)
*G06F 19/00* (2018.01)
(Continued)

(52) U.S. Cl.
CPC ....... *A61M 16/0057* (2013.01); *A61H 9/0007* (2013.01); *A61H 9/0078* (2013.01);
(Continued)

(58) Field of Classification Search
CPC .............. A61M 16/00; A61M 16/0003; A61M 16/0006; A61M 16/0009; A61M 16/0051;
(Continued)

(56) References Cited

U.S. PATENT DOCUMENTS

| 196,206 A | 10/1877 | Emery |
| 402,779 A | 5/1889 | Steinhoff |

(Continued)

FOREIGN PATENT DOCUMENTS

| CA | 2230622 A1 | 9/1998 |
| EP | 0054283 A2 | 5/1993 |

(Continued)

OTHER PUBLICATIONS

Birnkrant et al., "Noninvasive Ventilation During Gastrostomy Tube Placement in Patients with Severe Duchenne Muscular Dystrophy", Pediatric Pulmonology, 41, pp. 118-193, dated Feb. 2006.

(Continued)

*Primary Examiner* — Joseph D. Boecker
(74) *Attorney, Agent, or Firm* — Fay Sharpe LLP

(57) ABSTRACT

A combination respiratory therapy management system creates a combined respiratory therapy prescription that can be executed by a combined respiratory therapy device to provide multiple coordinated respiratory therapies to a patient. The system can update the combined respiratory therapy prescription and implement the updates while the combined respiratory therapy device is in use. Some versions of the system provide additional features that allow the combined respiratory therapy prescriptions to be created, accessed, shared with other users, and performed by the combination respiratory therapy device in a customizable user-friendly and non-threatening way.

11 Claims, 11 Drawing Sheets

(51) Int. Cl.
*A61H 9/00* (2006.01)
*A61M 16/06* (2006.01)
*A61H 31/00* (2006.01)
*A61M 16/16* (2006.01)
*A61M 16/10* (2006.01)

(52) U.S. Cl.
CPC ......... *A61H 31/00* (2013.01); *A61M 16/0006* (2014.02); *A61M 16/0009* (2014.02); *A61M 16/0051* (2013.01); *A61M 16/024* (2017.08); *G06F 19/3481* (2013.01); *A61H 2201/5012* (2013.01); *A61H 2201/5015* (2013.01); *A61H 2201/5048* (2013.01); *A61H 2201/5058* (2013.01); *A61H 2201/5071* (2013.01); *A61H 2201/5087* (2013.01); *A61M 16/0069* (2014.02); *A61M 16/06* (2013.01); *A61M 16/107* (2014.02); *A61M 16/1065* (2014.02); *A61M 16/16* (2013.01); *A61M 2016/0021* (2013.01); *A61M 2016/0027* (2013.01); *A61M 2016/0039* (2013.01); *A61M 2016/0042* (2013.01); *A61M 2205/18* (2013.01); *A61M 2205/3553* (2013.01); *A61M 2205/3561* (2013.01); *A61M 2205/3584* (2013.01); *A61M 2205/3592* (2013.01); *A61M 2205/50* (2013.01); *A61M 2205/505* (2013.01); *A61M 2205/52* (2013.01); *A61M 2205/581* (2013.01); *A61M 2205/583* (2013.01); *A61M 2205/80* (2013.01); *A61M 2209/08* (2013.01)

(58) Field of Classification Search
CPC .......... A61M 16/0057; A61M 16/0066; A61M 16/0069; A61M 16/022; A61M 16/024; A61M 16/06; A61M 2016/0018; A61M 2016/0021; A61M 2016/0027; A61M 2016/0036; A61M 2016/0039; A61M 2205/3344; A61M 2205/3553; A61M 2205/35615; A61M 2205/502; A61M 2205/581; A61M 2205/583; A61H 31/00; G06F 19/3481
See application file for complete search history.

(56) References Cited

U.S. PATENT DOCUMENTS

| | | |
|---|---|---|
| 1,044,031 A | 11/1912 | Drager |
| 1,150,238 A | 8/1915 | Winbray |
| 1,343,486 A | 6/1920 | Stolle |
| 1,358,893 A | 11/1920 | Stolle |
| 1,959,572 A | 5/1934 | Craig |
| 2,354,397 A | 6/1944 | Miller |
| 2,436,853 A | 3/1948 | Coleman |
| 2,588,192 A | 3/1952 | Akerman et al. |
| 2,626,601 A | 1/1953 | Riley |
| 2,762,366 A | 9/1956 | Huxley, III et al. |
| 2,772,673 A | 12/1956 | Huxley, III |
| 2,779,329 A | 1/1957 | Huxley, III et al. |
| 2,780,222 A | 2/1957 | Polzin et al. |
| 2,818,853 A | 1/1958 | Huxley, III et al. |
| 2,832,335 A | 4/1958 | Huxley, III et al. |
| 2,869,537 A | 1/1959 | Chu Chu |
| 2,914,064 A | 11/1959 | Sandelowsky |
| 3,043,292 A | 7/1962 | Mendelson |
| 3,063,444 A | 11/1962 | Jobst |
| 3,068,856 A | 12/1962 | Bird et al. |
| 3,083,707 A | 4/1963 | Seeler |
| 3,120,228 A | 2/1964 | Huxley, III |
| 3,291,122 A | 12/1966 | Engstrom et al. |
| 3,301,255 A | 1/1967 | Thompson |
| 3,310,050 A | 3/1967 | Goldfarb |
| 3,333,581 A | 8/1967 | Robinson et al. |
| 3,342,177 A | 9/1967 | Clementz |
| 3,426,794 A | 2/1969 | Freytag |
| 3,536,063 A | 10/1970 | Werding |
| 3,537,448 A | 11/1970 | Liston |
| 3,561,444 A | 2/1971 | Boucher |
| 3,566,862 A | 3/1971 | Schuh et al. |
| 3,584,621 A | 6/1971 | Bird |
| 3,630,196 A | 12/1971 | Bird et al. |
| 3,664,337 A | 5/1972 | Lindsey et al. |
| 3,682,166 A | 8/1972 | Jacobs |
| 3,683,655 A | 8/1972 | White et al. |
| 3,742,939 A | 7/1973 | Sayer |
| 3,760,801 A | 9/1973 | Borgeas |
| 3,766,914 A | 10/1973 | Jacobs |
| 3,802,417 A | 4/1974 | Lang |
| 3,857,385 A | 12/1974 | Hampl |
| 3,861,386 A | 1/1975 | Harris et al. |
| 3,896,794 A | 7/1975 | McGrath |
| 3,993,053 A | 11/1976 | Grossan |
| 4,020,834 A | 5/1977 | Bird |
| 4,054,134 A | 9/1977 | Kritzer |
| 4,051,843 A | 10/1977 | Franetzki et al. |
| 4,062,358 A | 12/1977 | Kritzer |
| 4,079,733 A | 3/1978 | Denton et al. |
| 4,133,305 A | 1/1979 | Steuer |
| 4,155,356 A | 5/1979 | Venegas |
| 4,182,599 A | 1/1980 | Eyrick et al. |
| 4,193,406 A | 3/1980 | Jinotti |
| 4,195,044 A | 3/1980 | Miller |
| 4,245,633 A | 1/1981 | Erceg |
| 4,263,907 A | 4/1981 | Lindsey |
| 4,265,237 A | 5/1981 | Schwanbom et al. |
| 4,311,135 A | 1/1982 | Brueckner et al. |
| 4,349,015 A | 9/1982 | Alferness |
| 4,397,306 A * | 8/1983 | Weisfeldt ............ A61H 9/0078 601/41 |
| 4,398,531 A | 8/1983 | Haystad |
| 4,424,806 A | 1/1984 | Newman |
| 4,429,688 A | 2/1984 | Duffy |
| 4,436,090 A | 3/1984 | Darling |
| 4,471,773 A | 9/1984 | Bunnell et al. |
| 4,546,764 A | 10/1985 | Gerber |
| 4,558,710 A | 12/1985 | Eichler |
| 4,592,349 A | 6/1986 | Bird |
| 4,601,465 A | 7/1986 | Roy |
| 4,621,621 A | 11/1986 | Marsalis |
| 4,635,857 A | 1/1987 | Hughes |
| 4,676,232 A | 6/1987 | Olsson et al. |
| 4,736,750 A | 4/1988 | Valdespino et al. |
| 4,747,402 A | 5/1988 | Reese et al. |
| 4,770,164 A | 9/1988 | Lach et al. |
| 4,805,613 A | 2/1989 | Bird |
| 4,815,452 A | 3/1989 | Hayek |
| 4,821,709 A | 4/1989 | Jesen |
| 4,823,784 A | 4/1989 | Bordoni et al. |
| 4,838,260 A | 6/1989 | Bird |
| 4,840,167 A | 6/1989 | Olsson |
| 4,867,151 A | 9/1989 | Bird |
| 4,886,057 A | 12/1989 | Nave |
| 4,928,674 A | 5/1990 | Halperin |
| 4,930,501 A | 6/1990 | Bird |
| 4,951,659 A | 8/1990 | Weiler et al. |
| 4,964,404 A | 10/1990 | Stone |
| 4,971,042 A | 11/1990 | Lerman |
| 4,973,047 A | 11/1990 | Norell |
| 4,977,889 A | 12/1990 | Budd |
| 4,981,295 A | 1/1991 | Belman et al. |
| 4,982,735 A | 1/1991 | Yagata et al. |
| 5,007,420 A | 4/1991 | Bird |
| 5,018,517 A | 5/1991 | Liardet |
| 5,027,809 A | 7/1991 | Robinson |
| 5,067,707 A | 11/1991 | Køhnke |
| 5,069,449 A | 12/1991 | Wardwell |
| 5,076,259 A | 12/1991 | Hayek |
| 5,101,808 A | 4/1992 | Kobayashi et al. |
| 5,107,830 A | 4/1992 | Younes |
| 5,109,839 A | 5/1992 | Blasdell et al. |
| 5,116,088 A | 5/1992 | Bird |
| 5,127,400 A | 7/1992 | DeVries et al. |

(56) References Cited

U.S. PATENT DOCUMENTS

| | | |
|---|---|---|
| 5,150,291 A | 9/1992 | Cummings et al. |
| 5,165,389 A | 11/1992 | Jing-Qi et al. |
| 5,165,398 A | 11/1992 | Bird |
| 5,193,529 A | 3/1993 | Labaere |
| 5,193,745 A | 3/1993 | Holm |
| 5,211,171 A | 5/1993 | Choromokos |
| 5,222,478 A | 6/1993 | Scarberry et al. |
| 5,261,394 A | 11/1993 | Mulligan et al. |
| 5,277,175 A | 1/1994 | Riggs et al. |
| 5,299,599 A | 4/1994 | Farmer et al. |
| 5,311,862 A | 5/1994 | Blasdell et al. |
| 5,322,057 A | 6/1994 | Raebe et al. |
| 5,345,930 A | 9/1994 | Cardinal et al. |
| 5,355,873 A | 10/1994 | Del Bon et al. |
| 5,390,665 A | 2/1995 | Leach |
| 5,398,676 A | 3/1995 | Press et al. |
| 5,415,190 A | 3/1995 | Ryder |
| 5,413,110 A | 5/1995 | Cummings et al. |
| 5,419,317 A | 5/1995 | Blasdell et al. |
| 5,423,313 A | 6/1995 | Olsson et al. |
| 5,439,430 A | 8/1995 | Rubens et al. |
| 5,451,190 A | 9/1995 | Liardet |
| 5,453,081 A | 9/1995 | Hansen |
| 5,479,920 A | 1/1996 | Piper et al. |
| 5,533,506 A | 7/1996 | Wood |
| 5,535,738 A | 7/1996 | Estes et al. |
| 5,542,416 A | 8/1996 | Chalvignac |
| 5,547,440 A | 8/1996 | Rubens et al. |
| 5,569,122 A | 10/1996 | Cegla |
| 5,570,682 A | 11/1996 | Johsnon |
| 5,596,983 A | 1/1997 | Zander et al. |
| 5,598,839 A | 2/1997 | Niles et al. |
| 5,606,754 A | 3/1997 | Hand et al. |
| 5,617,844 A | 4/1997 | King |
| 5,617,847 A | 4/1997 | Howe |
| 5,664,562 A | 9/1997 | Bourdon |
| 5,666,945 A | 9/1997 | Davenport |
| 5,679,797 A | 10/1997 | Kempf et al. |
| 5,694,919 A | 12/1997 | Rubsamen et al. |
| 5,713,349 A | 2/1998 | Keaney |
| 5,720,709 A | 2/1998 | Schnall |
| 5,741,237 A | 4/1998 | Walker |
| 5,791,340 A | 8/1998 | Schleufe et al. |
| 5,803,063 A * | 9/1998 | Corey ................ A61M 15/00 128/200.14 |
| 5,806,512 A | 9/1998 | Abramov et al. |
| 5,823,179 A | 10/1998 | Grychowski et al. |
| 5,829,429 A | 11/1998 | Hughes |
| 5,850,835 A | 12/1998 | Takaki et al. |
| 5,862,802 A | 1/1999 | Bird |
| 5,906,198 A | 5/1999 | Flickinger |
| 5,910,071 A | 6/1999 | Houyen |
| 5,937,857 A | 8/1999 | Caterini et al. |
| 5,938,117 A | 8/1999 | Ivri |
| 5,950,619 A | 9/1999 | Van Der Linden et al. |
| 5,964,223 A | 10/1999 | Baran |
| 5,970,974 A | 10/1999 | Van Der Linden et al. |
| 5,997,488 A | 12/1999 | Gelfand et al. |
| 6,030,353 A | 2/2000 | Van Brunt |
| 6,044,841 A | 4/2000 | Verdun et al. |
| 6,058,932 A | 5/2000 | Hughes |
| 6,066,101 A | 5/2000 | Johnson et al. |
| 6,068,602 A | 5/2000 | Tham et al. |
| 6,076,519 A | 6/2000 | Johnson |
| 6,076,520 A | 6/2000 | Cooper |
| 6,079,413 A | 6/2000 | Baran |
| 6,085,740 A | 7/2000 | Ivri et al. |
| 6,085,746 A | 7/2000 | Fox |
| 6,116,233 A | 9/2000 | Denyer et al. |
| 6,167,881 B1 | 1/2001 | Hughes |
| 6,176,235 B1 | 1/2001 | Benarrouch et al. |
| 6,209,540 B1 * | 4/2001 | Sugiura ............ A61M 16/0006 128/204.18 |
| 6,210,345 B1 * | 4/2001 | Van Brunt ........... A61H 9/0078 600/529 |
| 6,234,167 B1 | 5/2001 | Cox et al. |
| 6,240,919 B1 | 6/2001 | MacDonald et al. |
| 6,241,683 B1 | 6/2001 | Macklem et al. |
| 6,269,810 B1 | 8/2001 | Brooker et al. |
| 6,289,892 B1 | 9/2001 | Faithfull et al. |
| 6,302,105 B1 | 10/2001 | Wickham et al. |
| 6,336,455 B1 | 1/2002 | Howlett |
| 6,340,025 B1 | 1/2002 | Van Brunt |
| 6,355,002 B1 | 3/2002 | Faram et al. |
| 6,363,932 B1 | 4/2002 | Forchione et al. |
| 6,379,316 B1 | 4/2002 | Van Brunt et al. |
| 6,402,046 B1 | 6/2002 | Loser |
| 6,405,934 B1 | 6/2002 | Hess et al. |
| 6,410,414 B1 | 6/2002 | Lee |
| 6,412,481 B1 | 7/2002 | Bienvenu et al. |
| 6,415,791 B1 | 7/2002 | Van Brunt |
| 6,425,393 B1 | 7/2002 | Lurie et al. |
| 6,427,690 B1 | 8/2002 | McCombs et al. |
| 6,427,691 B1 | 8/2002 | Jinnoti |
| 6,435,175 B1 | 8/2002 | Stenzler |
| 6,450,154 B1 | 9/2002 | Choi |
| 6,450,163 B1 | 9/2002 | Blacker et al. |
| 6,467,476 B1 | 10/2002 | Ivri et al. |
| 6,526,976 B1 | 3/2003 | Baran |
| 6,540,153 B1 | 4/2003 | Ivri |
| 6,543,446 B1 | 4/2003 | Christopher |
| 6,546,927 B2 | 4/2003 | Litherland et al. |
| 6,550,472 B2 | 4/2003 | Litherland et al. |
| 6,550,476 B1 | 4/2003 | Ryder |
| 6,557,549 B2 | 5/2003 | Schmidt et al. |
| 6,568,387 B2 | 5/2003 | Davenport et al. |
| 6,571,790 B1 | 6/2003 | Weinstein |
| 6,581,596 B1 | 6/2003 | Truitt et al. |
| 6,581,598 B1 | 6/2003 | Foran et al. |
| 6,581,600 B2 | 6/2003 | Bird |
| 6,588,421 B1 | 7/2003 | Diehl et al. |
| 6,588,422 B1 | 7/2003 | Berthon-Jones et al. |
| 6,595,203 B1 | 7/2003 | Bird |
| 6,598,603 B1 | 7/2003 | Andersson et al. |
| 6,609,517 B1 | 8/2003 | Estes et al. |
| 6,612,303 B1 | 9/2003 | Grychowski et al. |
| 6,615,831 B1 | 9/2003 | Tuitt et al. |
| 6,626,175 B2 | 9/2003 | Jafari et al. |
| 6,631,721 B1 | 10/2003 | Salter et al. |
| 6,637,434 B2 | 10/2003 | Noble |
| 6,640,806 B2 | 11/2003 | Yurko |
| 6,644,304 B2 | 11/2003 | Grychowski et al. |
| 6,644,310 B1 | 11/2003 | Delache et al. |
| 6,644,311 B1 | 11/2003 | Truitt et al. |
| 6,663,574 B2 | 12/2003 | Faram et al. |
| 6,679,258 B1 | 1/2004 | Strom |
| 6,694,969 B1 | 2/2004 | Heinonen et al. |
| 6,702,998 B2 | 3/2004 | Conner |
| 6,708,688 B1 | 3/2004 | Rubin et al. |
| 6,708,690 B1 | 3/2004 | Hete et al. |
| 6,718,969 B1 | 4/2004 | Rubin et al. |
| 6,722,362 B2 | 4/2004 | Hete et al. |
| 6,727,042 B2 | 5/2004 | Rabinowski et al. |
| 6,729,327 B2 | 5/2004 | McFarland, Jr. |
| 6,729,334 B1 | 5/2004 | Baran |
| 6,752,151 B2 | 6/2004 | Hill |
| 6,776,159 B2 | 8/2004 | Pelerossi et al. |
| 6,789,538 B2 | 9/2004 | Wright et al. |
| 6,789,540 B1 | 9/2004 | Lin |
| 6,805,118 B2 | 10/2004 | Brooker et al. |
| 6,805,120 B1 | 10/2004 | Jeffrey et al. |
| 6,823,866 B2 | 11/2004 | Jafari et al. |
| 6,848,443 B2 | 2/2005 | Schmidt et al. |
| 6,851,425 B2 | 2/2005 | Jaffre et al. |
| 6,854,462 B2 | 2/2005 | Berthon-Jones et al. |
| 6,860,265 B1 | 3/2005 | Emerson |
| 6,860,270 B2 | 3/2005 | Sniadach |
| 6,880,556 B2 | 4/2005 | Uchiyama et al. |
| 6,904,906 B2 | 6/2005 | Salter et al. |
| 6,907,881 B2 | 6/2005 | Suki et al. |
| 6,910,479 B1 | 6/2005 | Van Brunt |
| 6,915,803 B2 | 8/2005 | Estes et al. |
| 6,948,497 B2 | 9/2005 | Zdrojkowski et al. |
| 6,968,840 B2 | 11/2005 | Smith et al. |

(56) References Cited

U.S. PATENT DOCUMENTS

| | | |
|---|---|---|
| 6,997,186 B2 | 2/2006 | Robertson et al. |
| 7,011,091 B2 | 3/2006 | Hill et al. |
| 7,013,894 B2 | 3/2006 | McFarland, Jr. |
| 7,032,596 B2 | 4/2006 | Thompson et al. |
| 7,036,500 B2 | 5/2006 | Niles et al. |
| 7,059,324 B2 | 6/2006 | Pelerossi et al. |
| 7,066,176 B2 | 6/2006 | Jaffe et al. |
| 7,070,761 B2 | 7/2006 | Rabinowitz et al. |
| 7,077,133 B2 | 7/2006 | Yagi et al. |
| 7,096,866 B2 | 8/2006 | Be'eri et al. |
| 7,100,607 B2 | 9/2006 | Zdrojkowski et al. |
| 7,124,755 B2 | 10/2006 | Van Hooser |
| 7,128,069 B2 | 10/2006 | Farrugia et al. |
| 7,131,439 B2 | 11/2006 | Blacker et al. |
| 7,165,547 B2 | 1/2007 | Truitt et al. |
| 7,188,624 B2 | 3/2007 | DeVries et al. |
| 7,191,776 B2 | 3/2007 | Niles et al. |
| 7,191,780 B2 | 3/2007 | Faram |
| 7,204,245 B2 | 4/2007 | Johnson et al. |
| 7,210,480 B2 | 5/2007 | Lurie et al. |
| 7,219,670 B2 | 5/2007 | Jones, Jr. et al. |
| 7,222,623 B2 | 5/2007 | De'Vries et al. |
| 7,232,417 B2 | 6/2007 | Plante |
| 7,302,949 B2 | 12/2007 | Pelerossi et al. |
| 7,311,096 B2 | 12/2007 | Gallops, Jr. |
| 7,445,607 B2 | 11/2008 | Plante |
| 7,469,700 B2 | 12/2008 | Baran |
| 7,500,481 B2 | 3/2009 | Delache et al. |
| 7,556,043 B2 | 7/2009 | Ho et al. |
| 7,562,657 B2 | 7/2009 | Blanch et al. |
| D597,659 S | 8/2009 | Chandran et al. |
| 7,594,508 B2 | 9/2009 | Doyle |
| 7,600,511 B2 | 10/2009 | Power et al. |
| 7,699,054 B2 | 4/2010 | Pelerossi et al. |
| 7,918,222 B2 | 4/2011 | Chen |
| 8,277,399 B2 | 10/2012 | Hamilton |
| 8,460,223 B2 | 6/2013 | Huster |
| 8,844,530 B2 | 9/2014 | Birnkrant |
| 2003/0015200 A1* | 1/2003 | Hansen ............... A61M 16/026 128/204.18 |
| 2003/0024533 A1 | 2/2003 | Sniadach |
| 2003/0051731 A1 | 3/2003 | Be'eri et al. |
| 2003/0075182 A1 | 4/2003 | Heidermann et al. |
| 2003/0140921 A1 | 7/2003 | Smith et al. |
| 2003/0140925 A1 | 7/2003 | Sapienza et al. |
| 2003/0145849 A1 | 8/2003 | Drinan et al. |
| 2003/0154980 A1 | 8/2003 | Berthon-Jones et al. |
| 2003/0183226 A1 | 10/2003 | Brand et al. |
| 2003/0205229 A1 | 11/2003 | Crockford et al. |
| 2004/0172222 A1* | 9/2004 | Simpson ............. G06F 19/3418 702/189 |
| 2005/0011523 A1* | 1/2005 | Aylsworth ............ A61M 16/00 128/207.18 |
| 2005/0039749 A1* | 2/2005 | Emerson ........... A61M 16/0006 128/204.23 |
| 2005/0051174 A1* | 3/2005 | Emerson ........... A61M 16/0057 128/207.14 |
| 2005/0056282 A1 | 3/2005 | Robertson et al. |
| 2005/0076913 A1 | 4/2005 | Ho et al. |
| 2005/0109340 A1 | 5/2005 | Tehrani |
| 2005/0139220 A1 | 6/2005 | Christopher |
| 2005/0150489 A1 | 7/2005 | Dunfield et al. |
| 2005/0165334 A1* | 7/2005 | Lurie .................... A61M 16/06 601/44 |
| 2005/0172954 A1 | 8/2005 | Smith et al. |
| 2005/0217666 A1 | 10/2005 | Fink et al. |
| 2005/0217675 A1 | 10/2005 | Thompson et al. |
| 2005/0263157 A1 | 12/2005 | Olsen |
| 2006/0000475 A1 | 1/2006 | Matthews et al. |
| 2006/0124131 A1 | 6/2006 | Chandran et al. |
| 2006/0130845 A1 | 6/2006 | Schegerin |
| 2006/0144398 A1 | 7/2006 | Doshi et al. |
| 2006/0178245 A1 | 8/2006 | Schiller et al. |
| 2006/0201500 A1 | 9/2006 | Von Hollen et al. |
| 2006/0243274 A1 | 11/2006 | Lieberman et al. |
| 2006/0249158 A1 | 11/2006 | Dhuper et al. |
| 2006/0272642 A1 | 12/2006 | Chalvignac |
| 2007/0017522 A1 | 1/2007 | Be-Eri et al. |
| 2007/0017523 A1 | 1/2007 | Be-Eri et al. |
| 2007/0089720 A1 | 4/2007 | Takahashi |
| 2007/0089749 A1 | 4/2007 | Ho et al. |
| 2007/0186928 A1* | 8/2007 | Be'Eri ................. A61M 16/00 128/204.18 |
| 2007/0199566 A1* | 8/2007 | Be'Eri ............. A61M 16/0051 128/204.23 |
| 2007/0272247 A1 | 11/2007 | Poral |
| 2007/0272248 A1 | 11/2007 | Lin |
| 2007/0272249 A1 | 11/2007 | Chandran et al. |
| 2008/0000477 A1* | 1/2008 | Huster ................... A61B 34/25 128/204.23 |
| 2008/0015456 A1 | 1/2008 | McCawley et al. |
| 2008/0021355 A1* | 1/2008 | Huster ................. A61H 9/0078 601/149 |
| 2008/0091117 A1 | 4/2008 | Choncholas et al. |
| 2008/0092895 A1 | 4/2008 | Birnkrant |
| 2008/0142014 A1 | 6/2008 | Jiang |
| 2008/0149099 A1* | 6/2008 | Doyle .................... A61H 31/02 128/202.12 |
| 2008/0190429 A1 | 8/2008 | Tatarek |
| 2008/0283060 A1 | 11/2008 | Bassin |
| 2009/0014001 A1* | 1/2009 | Myklebust ............ A61M 16/12 128/204.18 |
| 2009/0020121 A1 | 1/2009 | Bassin |
| 2010/0122699 A1* | 5/2010 | Birnkrant ............ A61M 1/0023 128/204.21 |
| 2010/0180897 A1* | 7/2010 | Malgouyres ........ A61M 16/024 128/204.23 |
| 2010/0319691 A1* | 12/2010 | Lurie .................... A61H 31/02 128/203.12 |
| 2011/0098612 A1 | 4/2011 | Lurie |
| 2011/0100360 A1 | 5/2011 | Faram |
| 2011/0125068 A1* | 5/2011 | Hansen ................... A61H 23/04 601/41 |
| 2011/0220107 A1* | 9/2011 | Kimm ................... A61M 16/00 128/204.21 |
| 2012/0016179 A1 | 1/2012 | Paradis |
| 2012/0083705 A1* | 4/2012 | Yuen .................... A61B 5/0002 600/508 |
| 2015/0027444 A1* | 1/2015 | Col, Jr. ............. A61M 16/0051 128/204.21 |
| 2015/0231348 A1* | 8/2015 | Lee ....................... A61N 1/3601 128/204.22 |

FOREIGN PATENT DOCUMENTS

| | | |
|---|---|---|
| GB | 23021 | 3/1914 |
| JP | 5096007 | 5/1993 |
| JP | 10165505 | 6/1998 |
| NZ | 223225 A | 4/1989 |
| RU | 1247009 A1 | 1/1995 |
| WO | WO 2004108199 A1 | 12/2004 |
| WO | WO 2007054829 A2 | 5/2007 |
| WO | WO 2008008659 A2 | 1/2008 |
| WO | WO 2008051816 A2 | 5/2008 |
| WO | WO 2010057166 A1 | 5/2010 |

OTHER PUBLICATIONS

Caramez et al., "Open Lung Approach (OLA) Using Conventional Mechanical Ventilation (CMV) or High Frequency Oscillation (HFO) Improves Oxygenation and Compliance in Ards Better than the Ardsnet Protocol", Abstract, Published Nov. 2006, Respiratory Care, vol. 51, No. 11, presented at Dec. 2008 Convention.

Four pages, Pediatric Advanced Life Support Textbook from the American Heart Associate including paged 4-10 and 4-11, dated 1994.

Four page web printout from http://www.ambu.com/RespiratoryCare/Respiratory_Care aspx?GID=GROUP51 & Product . . . date unknown, printed on Jan. 30, 2009, Ambu Mark IV—Reusable Resuscitator.

(56) References Cited

OTHER PUBLICATIONS

One page printout from http://www.laerdaltraining.com/isr/, Laerdal, date unknown, printed Apr. 16, 2009.
Printout from http://www.nagelnetwork.com/mouth.htm. 4 pgs, Mouthpieces, Flow Sensors, & Noseclips printed Nov. 11, 2009.
Birnkrant et al., "Use of Laryngeal Mask Airway in Patients with Severe Muscular Dystophy who Require Sedation or Anesthesia," Pediatric Pulmonology 41, pp. 1007-1081, published Nov. 2006.

* cited by examiner

COMBINATION RESPIRATORY THERAPY DEVICE, SYSTEM AND METHOD

CROSS-REFERENCE TO RELATED APPLICATIONS

This application is a continuation of U.S. patent application Ser. No. 13/692,192 filed Dec. 3, 2012, now U.S. Pat. No. 9,795,752, which is incorporated by reference herein in its entirety.

BACKGROUND

Patients with neuromuscular weakness as a result of strokes, spinal cord injuries, head trauma, or diseases such as muscular dystrophy and amyotrophic lateral sclerosis (ALS, or Lou Gehrig's disease) have an increased risk of morbity and mortality due to a weak cough and shallow breathing (hypoventilation). The number of chronic illnesses that cause weak cough and impaired lung ventilation is large and expanding.

When a patient has an ineffective cough, chest secretions are retained in the respiratory system, causing pneumonia, lung collapse, or, where the mucus fills the windpipe, fatal respiratory arrest. Additionally, shallow breathing causes low oxygen levels and high carbon dioxide levels in the patient's bloodstream, resulting in a medically fragile state of chronic respiratory failure in which even a common cold can result in severe respiratory illness. For these reasons, pulmonary complications are viewed as a major cause of morbidity and death in patients that have neuromuscular weakness.

As a patient's condition worsens, it becomes more likely that the patient will need both cough assistance and assisted ventilation. Respiratory therapies for addressing a weak cough often involve devices that provide assisted coughing via mechanical insufflation/exsufflation, while shallow breathing is commonly addressed by a separate, mechanical ventilation device.

SUMMARY

According to at least one aspect of this disclosure, a combination respiratory therapy prescription creator embodied in one or more machine-accessible storage media is executable by a computing device to receive data indicating a respiratory condition of a person; determine, based on the respiratory condition, a combination of pre-defined respiratory therapies from a plurality of possible therapies, the possible therapies including lung ventilation, lung volume recruitment, mucus extraction, and mucus mobilization therapies; select a combination respiratory therapy device from a family of combination respiratory therapy devices based on the determined combination of therapies, where each of the combination respiratory therapy devices includes a plurality of separate interfaces that are engageable with the person to provide a combination of lung ventilation therapy or lung volume recruitment therapy and mucus extraction therapy or mucus mobilization therapy; and based on the respiratory condition, create a respiratory therapy prescription to be executed by the selected combination respiratory therapy device without disengaging the selected combination respiratory therapy device from the person, the respiratory therapy prescription specifying at least a lung ventilation or a lung volume recruitment therapy and a mucus extraction therapy and/or a mucus mobilization therapy to be provided by the selected combination respiratory therapy device to the person.

The combination respiratory therapy prescription creator may be executable by a computing device to define a treatment session to be executed by the selected combination respiratory therapy device, where the treatment session includes a treatment sequence and the treatment sequence includes a mucus extraction therapy substantially immediately followed by a lung ventilation therapy or a lung volume recruitment therapy.

The combination respiratory therapy prescription creator may specify a number of times the treatment sequence is to be repeated during the treatment session and define a duration of the treatment session based on the number of times the treatment sequence is to be repeated. The combination respiratory therapy prescription creator may define a time at which the mucus mobilization therapy is to be executed by the selected combination respiratory therapy device prior to the execution of the treatment session. The combination respiratory therapy prescription creator may define a time at which another lung ventilation or lung volume recruitment therapy is to be executed by the selected combination respiratory therapy device after the execution of the treatment session. The combination respiratory therapy prescription creator may define another treatment session to be executed by the selected combination respiratory therapy device prior to the execution of the treatment session. The other treatment session may include a different treatment sequence.

The combination respiratory therapy prescription creator may define a treatment session to be executed by the selected combination respiratory therapy device, where the treatment session includes a plurality of treatment sequences and each treatment sequence includes a mucus extraction therapy substantially immediately followed by a lung ventilation therapy or a lung volume recruitment therapy. The combination respiratory therapy prescription creator may define the mucus extraction therapy as a plurality of cough cycles that are consecutively repeated by the selected combination respiratory therapy device and define each cough cycle as including an application of positive-pressure air flow by the selected combination respiratory therapy device followed by an application of negative-pressure air flow by the selected combination respiratory therapy device. The combination respiratory therapy prescription creator may define a duration of time for which the lung ventilation therapy or lung volume recruitment therapy is performed by the selected combination respiratory therapy device.

The combination respiratory therapy prescription creator may specify an audio message to be played by the selected combination respiratory therapy device at a time prior to the combination respiratory therapy device performing the combination respiratory therapy prescription. The combination respiratory therapy prescription creator may associate a digital graphic or animation of a user-selected mascot with the audio message.

The combination respiratory therapy prescription creator may receive data relating to a change in the person's respiratory condition and modify the respiratory therapy prescription based on the data relating to the change in the person's respiratory condition. The combination respiratory therapy prescription may define a treatment session to be performed by the selected combination respiratory therapy device, define a time interval after which the treatment session is to be performed, receive data relating to a change in the person's respiratory condition, and change the time interval based on the data relating to the change in the person's respiratory condition. The combination respiratory therapy prescription creator may define a treatment session to be performed by the selected combination respiratory therapy device, where the treatment session comprises a treatment sequence and the treatment sequence comprises a mucus extraction therapy followed by a lung ventilation therapy or a lung volume recruitment therapy; receive data relating to a change in the person's respiratory condition; and add a mucus mobilization therapy to the respiratory therapy prescription based on the change in the person's respiratory condition. The combination respiratory therapy prescription creator may define a treatment session to be performed by the selected combination respiratory therapy device, where the treatment session comprises a treatment sequence and the treatment sequence comprises a mucus extraction therapy followed by a lung ventilation therapy or a lung volume recruitment therapy; receive data relating to a change in the person's respiratory condition; and add another lung ventilation therapy or lung volume recruitment therapy following the treatment session based on the change in the person's respiratory condition. The combination respiratory therapy prescription creator may define a treatment session to be performed by the selected combination respiratory therapy device, where the treatment session comprises a treatment sequence and the treatment sequence comprises a mucus extraction therapy followed by a lung ventilation therapy or a lung volume recruitment therapy; receive data relating to a change in the person's respiratory condition; and increase an inspiratory pressure associated with the mucus extraction therapy based on the change in the person's respiratory condition.

The combination respiratory therapy prescription creator may define a treatment session to be performed by the selected combination respiratory therapy device, where the treatment session includes a treatment sequence and the treatment sequence includes a mucus extraction therapy followed by a lung ventilation therapy or a lung volume recruitment therapy; receive data relating to a change in the person's respiratory condition; and increase an expiratory pressure associated with the mucus extraction therapy based on the change in the person's respiratory condition.

The combination respiratory therapy prescription creator may define a treatment session to be performed by the selected combination respiratory therapy device, where the treatment session includes a treatment sequence to be repeated a number of times during the treatment session and the treatment sequence includes a mucus extraction therapy followed by a lung ventilation therapy or a lung volume recruitment therapy; receive data relating to a change in the person's respiratory condition; and increase the number of times the treatment sequence is to be repeated based on the change in the person's respiratory condition. The combination respiratory therapy prescription creator may receive data relating to a change in the person's respiratory condition and select a different combination respiratory therapy device from the family of combination respiratory therapy devices based on the data relating to the change in the person's respiratory condition.

The combination respiratory therapy prescription creator may electronically communicate the respiratory therapy prescription to a mobile device configured for use by a respiratory therapist. The combination respiratory therapy prescription creator may electronically communicate the respiratory therapy prescription to a device configured for use by the person. The combination respiratory therapy prescription creator may present an interactive graphical depiction of the respiratory therapy prescription at the computing device. The interactive graphical depiction may include a 24-hour timeline and one or more interactive slide bars to adjust the duration of portions of the respiratory therapy prescription along the timeline. The interactive graphical depiction may include an animated simulation of at least a portion of the respiratory therapy prescription, and the animated simulation may include a graphical depiction of at least a portion of human lungs receiving the simulated portion of the respiratory therapy prescription.

The combination respiratory therapy prescription creator may electronically communicate the respiratory therapy prescription to the selected combination respiratory therapy device for automated execution by the selected combination respiratory therapy device. The combination respiratory therapy prescription creator may receive the respiratory therapy prescription from the computing device at a mobile device configured for use by a respiratory therapist and electronically communicate the respiratory therapy prescription from the mobile device to the selected combination respiratory therapy device.

According to at least one aspect of this disclosure, a combined respiratory therapy device control module embodied in one or more machine-accessible storage media is executable by a combination respiratory therapy device controller to monitor a period of time over which a person connected to a combination respiratory therapy device controlled by the combination respiratory therapy device controller is to receive combined respiratory therapy according to a combined respiratory therapy prescription, where the combined respiratory therapy prescription defines a plurality of different therapy sessions to be performed by the combination respiratory therapy device at different times during the period of time, and each of the plurality of different therapy sessions comprising at least a mucus extraction therapy followed substantially immediately by a lung ventilation therapy or a lung volume recruitment therapy; configure the combination respiratory therapy device to perform each of the plurality of different therapy sessions at the appropriate times and with the appropriate device settings according to the combined respiratory therapy prescription; and control the combination respiratory therapy device to perform each of the plurality of different therapy sessions at the appropriate times with the appropriate device settings according to the combined respiratory therapy prescription.

The control module may repeat the mucus extraction therapy followed substantially immediately by the lung ventilation therapy or lung volume recruitment therapy a predefined number of times during each treatment session. The control module may present an audio message to the person before performing the therapy sessions. The control module may present the audio message at a predetermined time in relation to the therapy sessions. The control module may configure the audio message for the person based on the person's age. The control module may configure the audio message based on the time of day.

The control module may configure the combination respiratory therapy device to supply positive-pressure air flow at a first pressure followed positive-pressure air flow at a second pressure during the lung ventilation or lung volume recruitment therapy, and configure the combination therapy device to supply positive-pressure air flow at a third pressure greater than the first pressure followed by negative-pressure air flow during the mucus extraction therapy. The control module may configure the combination respiratory therapy device to supply a series of air pulses prior to at least one of the therapy sessions. The control module may receive user input, reconfigure the combination respiratory therapy device based on the user input, and perform a modified therapy session based on the user input.

According to at least one aspect of this disclosure, a combined respiratory therapy system includes a combination respiratory therapy device to execute a combined respiratory therapy prescription, where the combined respiratory therapy prescription defines a plurality of different therapy sessions to be performed by the combination respiratory therapy device over a period of time, each of the plurality of different therapy sessions includes at least a mucus extraction therapy followed substantially immediately by a lung ventilation therapy or a lung volume recruitment therapy; a prescription creator module embodied in one or more machine-accessible storage media, the prescription creator module executable by a computing system to interact with a physician to create the combined respiratory prescription; and a control module embodied in one or more machine-accessible storage media, the control module executable by the computing system to configure the combination respiratory therapy device to perform the therapy sessions according to the combined respiratory therapy prescription.

The system may include a data sharing module embodied in one or more machine-accessible storage media, and the data sharing module may electronically communicate the combined respiratory therapy prescription to the combination respiratory therapy device. The data sharing module may electronically communicate the combined respiratory therapy prescription to another computing device. The data sharing module may display at least a portion of the combined respiratory therapy prescription at another computing device used by healthcare personnel. The data sharing module may electronically communicate at least a portion of the combined respiratory therapy prescription from a remote computing device used by healthcare personnel to the combination respiratory therapy device. The data sharing module may display at least a portion of the combined respiratory therapy prescription at another computing device used by a person receiving the combined respiratory therapy. The data sharing module may electronically communicate at least a portion of the combined respiratory therapy prescription from a computing device used by a person receiving the combined respiratory therapy to the combination respiratory therapy device. The data sharing module may enable two-way electronic communication of at least a portion of the combined respiratory therapy prescription between or among a plurality of computing devices used by a plurality of healthcare personnel.

According to at least one aspect of this disclosure, a control unit for a combination respiratory therapy device includes an air supply; a first air circuit operably coupled to the air supply to supply positive-pressure air flow to a positive air flow patient interface of the combination respiratory therapy device; a second air circuit operably coupled to the air supply to supply negative-pressure air flow to a negative air flow patient interface of the combination respiratory therapy device; the second air circuit being physically separate from the first air circuit; a controller to control the air supply; and memory accessible by the controller, the memory including instructions executable by the controller to activate the air supply to supply air to the first air circuit at a first positive pressure during a ventilation or lung volume recruitment portion of a respiratory therapy treatment session; and alternatingly activate the air supply to supply air to the first air circuit at a second positive pressure greater than the first positive pressure followed by a supply of air to the second air circuit at a negative pressure during a coughing assistance portion of the respiratory therapy treatment session.

The control unit may include another air supply and a third air circuit operably coupled to the other air supply to supply a series of air pulses to an air pulse patient interface of the combination respiratory therapy device. The third air circuit may be physically separate from at least the second air circuit. The third air circuit may be physically separate from the first air circuit and the second air circuit. The air pulse patient interface may be selectively coupled to the positive air flow patient interface. The control unit may include a control panel to input patient condition information, where the control unit may be configured to adjust the operation of the air supply in real time based on the patient condition information. The positive air flow patient interface may supply positive air flow nasally and the negative air flow interface may supply negative air flow orally. The control unit may include one or more sensors in communication with the controller to align the positive air flow with a person's normal breathing pattern during both the coughing assistance portion and the ventilation portion of the respiratory therapy treatment session.

A system for combination respiratory therapy may include any of the foregoing control units, the positive air flow patient interface, and the negative air flow patient interface. The control unit may be in selective communication with an air pulse patient interface. The instructions may be configured to selectively provide, during the respiratory therapy treatment session: mucus extraction therapy followed by lung ventilation therapy; or mucus extraction therapy followed by lung volume recruitment therapy; or mucus mobilization therapy followed by mucus extraction therapy followed by lung ventilation therapy; or mucus mobilization therapy followed by mucus extraction therapy followed by lung volume recruitment therapy. The system may include a network interface to receive user input relating to a patient's condition from another device. The system may include a graphical user interface to create or modify the respiratory therapy prescription, and the graphical user interface may be located at the controller. The system may include an audio user interface to provide audio messages to a person using the combination respiratory therapy device.

BRIEF DESCRIPTION OF THE DRAWINGS

This disclosure is illustrated by way of example and not by way of limitation in the accompanying figures. The figures may, alone or in combination, illustrate one or more embodiments of the disclosure. For simplicity and clarity of illustration, elements illustrated in the figures are not necessarily drawn to scale. For example, the dimensions of some elements may be exaggerated relative to other elements for clarity. Further, where considered appropriate, reference labels may be repeated among the figures to indicate corresponding or analogous elements.

DETAILED DESCRIPTION

Figure 1:
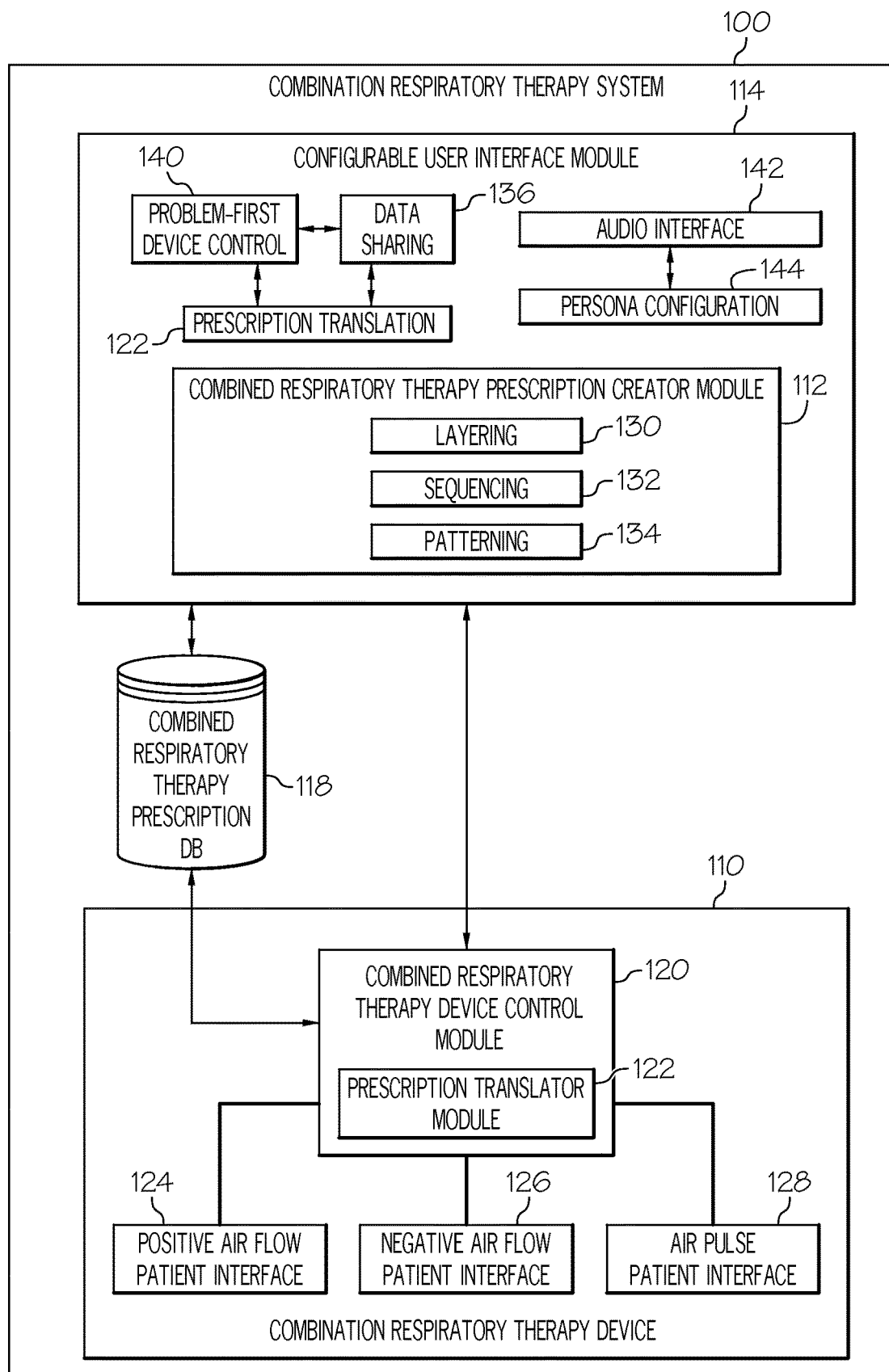
FIG. 1 is a simplified module diagram of at least one embodiment of a combination respiratory therapy management system.

While the concepts of the present disclosure are susceptible to various modifications and alternative forms, specific embodiments thereof are shown by way of example in the drawings and are described in detail below. It should be understood, however, that there is no intent to limit the concepts of the present disclosure to the particular forms disclosed, but on the contrary, the intention is to cover all modifications, equivalents, and alternatives consistent with the present disclosure and the appended claims.

Referring to FIG. 1, a system 100 for managing combined respiratory therapy provided to a person using a combination respiratory therapy device 110 includes a number of different pieces of computerized functionality, which for ease of discussion are represented herein as modules. Illustratively, these modules include a configurable user interface module 114 and a combined respiratory therapy device control module 120. In various embodiments of the system 100, the configurable user interface module 114 may include one or more other modules 112, 122, 130, 132, 134, 140, 142, 144. Each of the modules 114, 120, 112, 122, 130, 132, 134, 140, 142, 144 may be implemented as computer software, firmware, hardware, or a combination thereof, according to the requirements of a particular design or implementation of the system 100. Further, any or all of the modules 114, 120, 112, 122, 130, 132, 134, 140, 142, 144 may be implemented as part of the combination respiratory therapy device 110 in some embodiments (e.g., as a "standalone" system), while in other embodiments, some of the modules 114, 120, 112, 122, 130, 132, 134, 140, 142, 144 may be implemented on one or more other computing devices (e.g., mobile devices or more traditional desktop- or laptop-style computers). As described in more detail below, the configurable user interface modules 112, 122, 130, 132, 134, 140, 142, 144 can be selectively activated at the device 110 or at one or more other computing devices to facilitate interaction with and control of the combination device 110 by an authorized person or by different types of authorized persons. Such authorized persons may include clinicians (e.g., physicians), respiratory therapists, nurses, family members and other caregivers, as well as the patient receiving the combined respiratory therapy. For ease of discussion, any of such persons may be referred to herein as a "user" or "users" of the system 100.

The prescription creator module 112 enables a user (e.g., a clinician) to create a combined respiratory therapy prescription in a user-friendly way using, for example, graphical, audio, and/or video features. As such, the prescription creator module 112 alleviates the need for users to spend time learning how to use non-intuitive buttons, dials, or the like on a piece of therapy equipment that often has limited real estate for more sophisticated user interface features. A combined respiratory therapy prescription may include one or multiple integrated combinations of different respiratory therapies that are scheduled to occur at various times of the day. For example, in some embodiments, a combined respiratory therapy prescription integrates repeated cycles of cough assistance (e.g., mucus mobilization and/or mucus extraction therapy) with lung ventilation therapy and/or lung volume recruitment therapy. The combined respiratory therapy prescription can be translated into machine-readable instructions by the prescription translator module 122. Such instructions can be read and executed by hardware components (e.g., a microprocessor) of the combination device 110 to control the provision of combined respiratory therapy to the patient. Once created, the combined respiratory therapy prescription and/or the machine-readable version thereof may be stored in computer memory, for example, in a computerized data structure such as a combined respiratory therapy prescription database 118.

The stored combined respiratory therapy prescription or portions thereof can be accessed and viewed by the person who created the prescription or by other users (e.g., respiratory therapists, other clinicians, caregivers, or the patient) using the data sharing module 136. As such, the data sharing module 136 presents the combined respiratory therapy prescription in a format that is easy to understand and customizable by or for the particular user. In some embodiments, the data sharing module 136 may allow certain categories of authorized persons to view certain data or make certain types of changes to the combined respiratory therapy prescription. For example, a clinician may be permitted to view and change any aspect of the combined respiratory therapy prescription, while a therapist may be permitted to view the prescription but only change certain parts of the prescription (e.g., inspiratory or expiratory pressure within a limited defined range of pressures, or the therapy start time) but not others (e.g., the therapy duration). Similarly, limitations may be placed on a patient or family member's ability to view and change the combined respiratory therapy prescription.

In some embodiments, the user interface module 114 includes a problem-first device control module 140, which allows a user to make adjustments to the patient's therapy regimen while the therapy is in progress, whether in response to a change in the patient's condition observed by the user, or in response to some other triggering condition. For example, in some embodiments, the prescription translator module 122 may receive data from the combination device 110 while a therapy is in progress, such as the current status of the therapy or information about the patient's condition. Such data obtained from the device 110 can be displayed to the user in a human-understandable form using the data sharing module 136. Changes to the patient's therapy may be input by the user in response to the data obtained from the combination device 110, or in response to changes in the patient's condition observed by the caregiver, for example, using the problem-first device control module 140.

Further, in some embodiments, the user interface module 114 includes an audio interface module 142, and may also include a persona configuration module 144. The modules 142, 144 are designed to further enhance the human-device interaction. For example, the audio interface 142 may play pre-recorded human voice messages explaining how to use the device 110 or explaining a therapy that is about to begin. The persona configuration module 144 may allow the user to ascribe a "personality" to the device 110. For example, the persona configuration module 144 may allow the user to select a graphical or animated character and/or a particular tone of voice or accent to be used by the device 110 when communicating with the user. Thus, using the system 100, a combination respiratory therapy device 110 can be used to provide multiple integrated and coordinated respiratory therapies to a respiratory patient over a period of time, in a manner that is both intuitive and non-threatening to the user or the patient. Moreover, the various treatments specified by the respiratory therapy prescription can be customized and adjusted, even down to the breath by breath level, according to the patient's needs as they might change or progress. Such customizations and adjustments can be implemented responsively by the combination respiratory device 110.

The illustrative combination respiratory therapy device 110 is one of a family of combination respiratory therapy devices 110, each of which can be used to provide multiple integrated respiratory therapies. The combination device 110 includes a combined respiratory therapy control module 120, a positive-pressure air flow patient interface 124, a negative-pressure air flow patient interface 126, and, in some embodiments, an air pulse patient interface 128. The positive-pressure air flow patient interface 124 is designed to supply positive (e.g., inspiratory) pressure to a patient with whom the interface 124 is engaged. The negative-pressure air flow patient interface 126 is designed to supply negative (e.g., expiratory) pressure to a patient with whom the interface 126 is engaged. The air pulse patient interface 128 is designed to supply air pulses to a patient's airway, lungs or chest area to provide, for example, Continuous High Frequency Oscillation (CHFO), Continuous Positive Expiratory Pressure (CPEP), and/or High Frequency Chest Wall Oscillation (HFCWO).

The illustrative control module 120 interfaces with the prescription creator module 112 to obtain the user-defined and/or user-modified combined respiratory therapy prescription. A version of the prescription translator module 122 may be provided at the user interface level (e.g., as part of the configurable user interface module 114) and/or at the device level (e.g., as part of the control module 120) in various embodiments of the system 100. Whether at the user interface level or at the device level, the prescription translator module 122 converts the prescription into a machine-executable form that can be used to control the application of air flow to the patient via the interfaces 124, 126, 128 as needed. For example, where a prescription specifies a treatment session to include a cough cycle followed by lung ventilation, the prescription translator module 122 generates the device settings needed for the combination device 110 to perform the therapy session. Those device settings may include, for instance, specific air pressure levels, an indication of whether the air pressure is to be positive (e.g., inflation) or negative (e.g., suction), a duration of time to provide the airflow, a number of times to repeat the application of air pressure, etc. As an example, the device settings for a combined respiratory treatment sequence may include "cough: interface 124 on at +25 cm water, interface 126 on at −30 cm water; vent: interface 124 on at +15 cm water, interface 124 on at +4 cm water, time=2 minutes." The translator module 122 may further translate these device settings to specific "valve open" and "valve close" control signals that can be received and acted on directly by specific electromechanical components of the device 110.

Using the combination respiratory therapy device 110, the lung volume recruitment and lung ventilation therapies can be integrated with assisted cough cycles such that assisted ventilation or lung volume recruitment can be automatically coordinated (e.g., alternated) with assisted coughing on a breath to breath basis if needed. In this way, the mix of cough assistance and lung ventilation or lung volume recruitment therapy can be customized to each patient's needs. Further, the combination device 110 eliminates the need to apply two separate devices sequentially. Sequential therapy is difficult for sick or weak patients to tolerate and may cause the patient to become clinically unstable. Additionally, some embodiments of the combination device 110 are portable, such that they can be mounted or stored on a wheelchair, thereby increasing the patient's quality of life. Still further, in some embodiments, the inspiratory and expiratory air circuits of the device 110 are physically separated so that the positive pressure circuit remains clean and unobstructed. Further details of the illustrative combination device 110 are described below in connection with FIG. 3.

In more detail, the illustrative prescription creator module 112 utilizes a framework of standardized terminology to describe the combined respiratory therapy prescription. As such, the framework provides a vehicle by which combined respiratory therapy prescriptions can be easily created, understood, and shared by the various healthcare practitioners that may be involved in the patient's care. In that regard, the illustrative combined respiratory therapy prescription creator module 112 includes a layering module 130, a sequencing module 132, and a patterning module 134. The layering module 130 allows the caregiver to select an appropriate combination respiratory therapy device 110 simply by specifying (at a graphical user interface of the configurable interface module 114, for example) the different types or "layers" of therapy that the patient needs.

The layering module 130 automatically maps the therapy layers selected by the caregiver to one or more combination respiratory therapy devices 110 that are capable of providing those therapies. In the illustrated embodiments, the therapy layers include mucus mobilization, mucus extraction, lung volume recruitment, and lung ventilation therapy layers. Generally speaking, mucus mobilization refers to respiratory therapy that is intended to loosen chest secretions (e.g., mucus) so that the chest secretions may be extracted from the lungs by a normal or assisted cough. Mucus mobilization therapy often involves the mechanical application of air pulses, vibrations, or oscillations to the patient's airway, lungs, chest and/or back by a device such as THE VEST, or the METANEB device, both of which are available from the Hill-Rom Company, Inc.

Mucus extraction refers to therapy that mechanically assists the patient's natural ability to cough, or which mechanically removes secretions from the lungs for the patient, if the patient is unable to cough on his or her own. To perform mucus extraction therapy, the control module 120 may configure the combination device 110 to begin the therapy by providing an extra-large expanded breath (e.g., "deep lung insufflation"). This may involve the device 110 delivering an inspiratory pressure in the range of about 30%-50% above the "chronic" inspiratory pressure that the device 110 would normally use for ventilation or lung volume recruitment therapy.

The deep breaths provided by the combination device 110 during mucus extraction therapy are intended to maximize lung recoil (faster flow during exhalation) and may help expand any collapsed portions of the lung. But because they are big breaths, a patient can normally tolerate mucus extraction therapy only in limited "doses." During mucus extraction therapy, the control module 120 synchronizes the assisted inspiratory breath provided by the device 110 to the patient's inspiratory effort, so that the patient does not exhale during the inspiratory phase. The "deep insufflation" breath is followed by "active" exhalation or "exsufflation," during which suction (negative) pressure removes secretions from the airway. The control module 120 likewise synchronizes the suction (negative) pressure to the patient's expiratory phase of breathing. Accordingly, some forms of mucus extraction therapy that can be provided by the device 110 may be referred to as "mechanical insufflation/exsufflation." For mucus extraction, the inspiratory pressure may be set in the range of about +25 cm water and the expiratory pressure in the range of about −30 cm water, for example. Thus, a mucus extraction portion of the combined respiratory therapy prescription may be written as "+25/−30."

Lung ventilation refers to therapy that is intended to mechanically assist the patient with his or her normal breathing pattern, or to mechanically breathe for the patient, if the patient is unable to breathe on his or her own. Thus, lung ventilation therapy is generally applied in a continuous manner for a period of time (rather than in "cycles" like mucus extraction therapy). In the illustrated embodiments, in which they are integrated within a single combination respiratory therapy device 110, both mucus extraction and lung ventilation therapy include software control algorithms that synchronize the machine-generated breathing or mucus extraction with the patient's natural breathing pattern. Lung ventilation may be achieved by using the positive-pressure air flow patient interface 124 to deliver a higher positive pressure during the patient's inhalation and a lower positive pressure during exhalation. The difference between the inspiratory and expiratory pressure levels (the "span") is what ventilates the lungs. For lung ventilation, the inspiratory pressure may be set at +15 cm water and the expiratory pressure at +4 cm water. Thus, a lung ventilation portion of the combined respiratory therapy prescription may be written as "+15/+4."

To better achieve effective lung ventilation, the two positive pressure levels can be synchronized to the patient's breathing pattern. To do this, the combination respiratory therapy device 110 may detect a small, patient-generated negative "sniff pressure" or negative (inspiratory) flow to sense that the patient is starting inhalation ("wants a breath") and then the device may support that breath with the commanded inspiratory pressure. When the device 110 detects that the patient's inspiratory flow/pressure/effort tapers off, the device 110 can conclude that the patient is ready for exhalation and switch to the lower (expiratory) positive pressure setting (which may be known as the PEEP or positive end expiratory pressure).

In some embodiments, the control module 120 includes software that synchronizes the mechanically-assisted breathing provided by the device 110 to the patient's spontaneous breathing. For example, in some embodiments, the control module 120 may keep track of the patient's respiratory pattern over time, and use a prior respiratory pattern to predict a future respiratory pattern, in terms of rate of breathing, duration of inhalation, etc. In some embodiments, the flow waveform or "(chest) rise time" generated by the device 110 (how fast the device 110 achieves the set inspiratory pressure) during lung ventilation therapy may be adjustable according to the patient's needs or preferences (a slower rise time is gentler, but too slow may leave the patient breathless). The combination respiratory therapy device 110 may use the same or similar techniques as described above to synchronize mucus extraction (assisted coughing) to the patient's breathing pattern, in order to maximize the efficacy and comfort of mucus extraction therapy or for other reasons.

Additionally, when the combination device 110 is used for lung ventilation, the control module 120 can instruct the device 110 to provide a "backup" rate of breathing if the patient stops breathing on their own or is sedated, in which case the device 110 will deliver automatic breathing on a timer. Further, when the device 110 is used for lung ventilation, the control module 120 can initiate an alarm to alert caregivers if the interface 124 becomes disconnected from the patient (e.g., tubing is pulled away, nasal mask falls off, etc.). As such, the combination device 110 can selectively provide a number of different features depending on the type of therapy for which it is being used, where some features (such as backup breathing and alarms) may be applicable to some therapies but not others. The combination respiratory therapy device 110 may use the same or similar techniques as described above to automatically provide mucus extraction (assisted coughing) to a patient who is asleep, unconscious or sedated; for example, by providing mucus extraction automatically, on a timer, while a patient is asleep. Likewise, the control module 120 can initiate an alarm to alert caregivers if the negative airflow interface 126 becomes disconnected from the patient (e.g., falls out of the patient's mouth).

Lung volume recruitment refers to therapy that mechanically inflates the lungs episodically rather than continuously. When the combination device 110 applies positive pressure air flow for lung volume recruitment, the positive pressure inflates the lungs, and thus prevents them from collapsing. This may be done, for example, after each cough cycle of a daytime therapy session, to help the patient recover his or her breath before the next cough. Lung volume recruitment therapy may also be applied after an assisted cough therapy session has concluded, to "solidify" the lung volume improvements made during the assisted cough session and to help the patient recover from the assisted coughing. Thus, lung volume recruitment therapy may be used when a patient is awake and cooperative.

As compared to lung ventilation therapy, lung volume recruitment is generally less sophisticated. When performing lung volume recruitment therapy, the combination device 110 may synchronize the inspiratory pressure to the patient's breathing pattern, but there may not be a need for an expiratory pressure (PEEP). Since the patient is typically awake and assisting with the process during lung volume recruitment therapy, more advanced software algorithms to track the patient's breathing pattern or to provide a backup rate or alarms are generally not needed, as they would be for lung ventilation. For lung volume recruitment therapy, the inspiratory pressure may be set in the range of about +15 cm water and the expiratory pressure may be set in the range of about 0 cm water (e.g., exhaling to no added pressure). Thus, a lung volume recruitment portion of the combined respiratory therapy prescription may be written as "+15/0."

The sequencing module 132 allows the caregiver to define, customize, and modify the details of each respiratory therapy treatment session according to the patient's needs, where a "treatment session" generally refers to an instance or occurrence of a coordinated combination of respiratory therapies. A treatment session may include a number of sequentially-executed therapies, or treatment sequences that involve the repetition of one or more types of therapy (such as a treatment sequence made up of cough assistance followed by lung ventilation therapy). For example, the sequencing module 132 may be used to define or specify the positive and negative pressure settings that comprise each cough cycle; to define or specify the number of cough cycles that will be applied sequentially at the start of each treatment sequence; to define or specify the duration of lung volume recruitment or lung ventilation therapy to be applied substantially immediately after the specified number of cough cycles (e.g., without interruption) to complete each treatment sequence; and/or to define or specify the number of treatment sequences that, applied sequentially, may comprise a treatment session.

Figure 4:
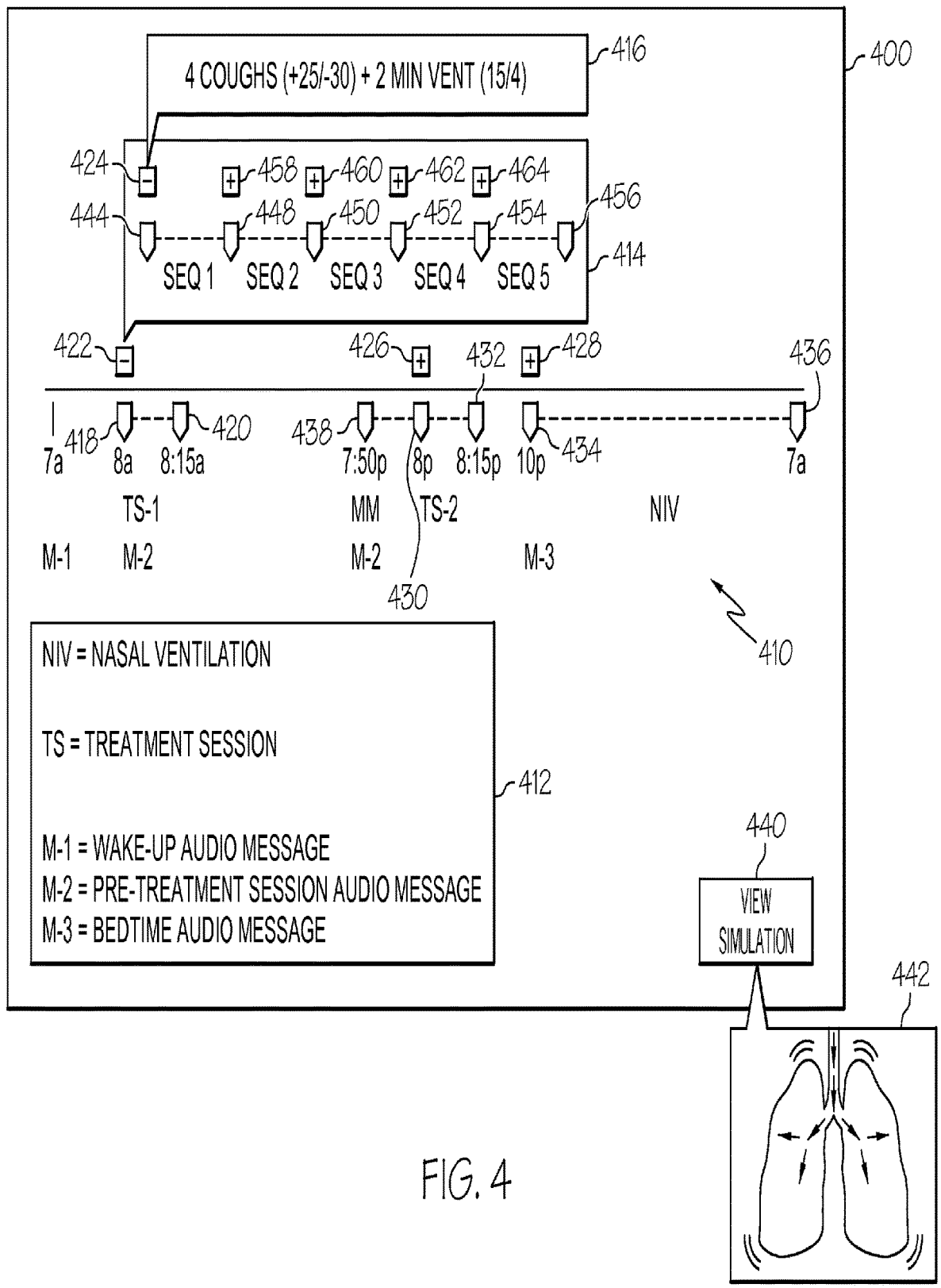
FIG. 4 is a simplified elevational view of at least one embodiment of a user interface for a prescription creator module of at least one embodiment of the system of FIG. 1.

The patterning module 134 allows the caregiver to define an entire pattern of respiratory care to be applied to the patient over a defined period of time (e.g., a 24-hour period), in real clock time. For example, a therapy pattern may include a treatment session comprised of a specific number of treatment sequences, as described above, which starts and ends in the morning; a similar treatment session that starts and ends in the evening, but is immediately preceded by a time period of mucus mobilization therapy; and a lung ventilation therapy session that starts at night, when the patient falls asleep, and ends in the morning, when the patient awakens. As such, the patterning module 134 allows the caregiver to specify that the combination device 110 begins or performs certain therapies at certain times of the day. In other words, the patterning module 134 can be used to associate specific start and stop times with the various coordinated therapies. The patterning module 134 can be used to illustrate a patient's specific layers of therapy and their inter-relationships in clock time. As such, the patterning module 134 can provide a useful tool for creating, modifying and sharing the combination respiratory therapy prescription among interested parties. Thus, in some embodiments, the patterning module 134 presents the pattern of respiratory therapy visually, e.g., as a graphical timeline or other visual representation of the patient's 24-hour respiratory care plan, at a user interface of the system 100. An illustrative example of one such visual representation is shown in FIG. 4, described below.

The configurable user interface module 114 includes a software-based user interface to the various modules 112, 122, 136, 140, 142, 144. For example, in embodiments that include the prescription creator module 112, the user interface module 114 includes a software-based user interface that allows a physician or other qualified health professional to create the combined respiratory therapy prescription and store the prescription (e.g., in the database 118) at a computing device of the system 100. In other embodiments, the user interface may alternatively or in addition, provide the user with access to the data sharing module 136, the problem-first device control module 140, and/or other modules of the system 100.

As noted above, the data sharing module 136 provides a communication interface by which a combined respiratory therapy prescription, or portions thereof, can be presented at a computing device of the system 100 used to create the combined respiratory therapy prescription to the combination device 110, or at another computing device, such as a mobile device used by a respiratory therapist responsible for the patient's care, or a computing device located near the patient or used by the patient (such as a personal computer or mobile computing device located in the patient's hospital room or in the patient's home). In some embodiments, the prescription is shared between or among devices using an electronic communication interface accessed by the data sharing module 136, which includes, for example, one or more input/output modules for data communication via a standard wired or wireless network interface (e.g., WIFI, cellular, Ethernet, etc.), one or more hard-wired communication ports (e.g., a Universal Standard Bus port or other port by which a flash drive or cable may be connected), or a combination thereof.

Whereas the prescription creation module 112 allows the combined respiratory therapy prescriptions to be created using a "user-friendly" interface and then transferred to the combination device 110 for execution, the illustrative data sharing module 136 enables specialized respiratory clinicians who are not at the patient's bedside to remotely change or update the patient's respiratory prescription, in order to respond in a timely manner to clinical changes in the patient's condition or for other reasons.

One illustrative example of a scenario in which the data sharing module 136 may be used is as follows. Using a computer on which the configurable user interface module 114 is configured to include the prescription creator module 112, e.g., the prescription creator module 112 is either installed or accessible via a network (e.g., the "cloud"), such as a hospital computer used to manage electronic medical records, a physician creates a combined respiratory therapy prescription. The layering module 130 automatically selects a combination device 110 to be used to implement the prescription. The patterning module 134 displays the chronological pattern of prescribed therapy in clock time. The sequencing module 132 generates the specific details of the treatment sequences that form the treatment sessions, including all of the requisite device settings for the selected combination device 110. As a result, the physician can, via the configurable user interface module 114, examine and adjust or modify the patient's combined respiratory prescription quickly and accurately, using, e.g., the hospital computer. Another version of the configurable user interface module 114, including the data sharing module 136, may be installed on another computer used by the physician, to allow the physician to view the combined respiratory prescriptions that he or she has created from a remote location, even from home.

Yet another version of the configurable user interface module 114, including the data sharing module 136, may be installed on a computer used by a respiratory therapist. With the data sharing module 136, the respiratory therapist reviews the combined respiratory therapy prescription (e.g., at a hospital computer) previously created by the physician. The computer may be a handheld device or the therapist may transfer the prescription to another computing device that is a handheld or "mobile" device (such as a smart phone, tablet computer, or personal digital assistant) on which another instance of the configurable interface module 114 or a simplified version thereof including the data sharing module 136 is installed.

Using the data sharing module 136, which may be installed directly on the handheld computing device or accessed via a network (e.g., the "cloud"), the therapist is able to plan his or her shift schedule by viewing the 24-hour prescription timelines (e.g., treatment patterns), and/or other details of the combined respiratory therapy prescriptions, for all of the patients under his or her care. Using the handheld device, the therapist can review the treatment plans at any time, whether the therapist is at the patient's bedside or at a distant location. With the data sharing module 136, the therapist's handheld device can be programmed to issue reminders that can help keep the therapist on schedule by generating an audio and/or visual alert at or in advance of the start time for the patient's next scheduled therapy. Also using the data sharing module 136, the therapist's handheld device may link to an electronic communication network (e.g., a hospital paging system, computer network, or telecommunications network), to alert the therapist when new combined respiratory therapy prescriptions are created or existing prescriptions are modified by other caregivers, for example. Further, using the data sharing module 136, new or updated combined respiratory therapy prescriptions can be transferred electronically (e.g., via a direct, hard-wired connection or over a wired or wireless network) to the therapist's handheld device (wherever it may be located) in real time or downloaded to the handheld device from, e.g., a hospital computer. When the therapist signs out from a shift, he or she can transfer the combined respiratory therapy prescriptions for the patients in his or her care to a handheld device used by the next therapist that is coming on duty, by linking the handheld devices using a wired or wireless (e.g., WIFI or Near Field Communication (NFC)) data communication connection.

When a patient is ready to change venues, e.g., to move to a different hospital or nursing home, or to return to the patient's own home, the data sharing module 136 can be used to send the patient's combined respiratory therapy prescription to the patient's new venue via wired or wireless data communication as described above. As the combined respiratory therapy prescription specifies the combination device 110 to be used to perform the combined respiratory therapy prescription, as well as the particular schedule and combination of respiratory therapies to be performed for the patient (including the device settings), the transfer of the prescription to a computing device located at the patient's new venue should enable the patient's respiratory care to be continued at the new location relatively seamlessly.

The illustrative problem-first device control module 140 interfaces with the prescription translation module 122 to directly implement changes to a patient's combined respiratory therapy prescription "on the fly," e.g., in real-time during the patient's therapy, according to the patient's preferences or as the patient's health condition changes. The problem-first device control module 140 includes computer logic and data (e.g., look-up tables or the like) that map various device settings of the combination device 110 to different clinical conditions. For example, the problem-first module 140 may derive triggering conditions and desired therapeutic changes from evidence-based guidelines or from the patient's own treatment history data (which may indicate therapies that have been successful or unsuccessful for the patient in the past). As such, the problem-first module 140 allows caregivers and others to modify the patient's combined respiratory therapy prescription simply by indicating the clinical change to the problem-first module 140. For example, a therapist may notice that his or her patient is currently unable to cough up secretions without assistance. In this scenario, the caregiver can input "unable to cough up secretions" to the problem-first module 140, using a graphical user interface provided by the configurable user interface module 114, for example. The prescription translation module 122 translates the clinical change into the appropriate device setting changes for the combination device 110. In embodiments where the problem-first module 140 is not integrated with the combination device 110, the data sharing module 136 transfers the device setting changes directly to the combination device 110, which implements the device setting changes. In other words, the problem-first device control module 140 enables direct, automatic prescription revision, without requiring the user to view or compose an entire prescription.

The illustrative problem-first device control module 140 can also allow the user to respond to data transmitted by the combination device 110, via the data sharing module 136. Based on changes in the data received from the combination device 110, which the caregiver may view using the data sharing module 136, for example, the caregiver may determine that adjustments to the patient's combined respiratory therapy prescription are needed, and implement those adjustments using the problem-first device control module 140 as described above.

One illustrative example of a scenario in which the problem-first device control module 140 may be used is as follows. Suppose a home care company receives a new patient who had been discharged from the hospital. Using the data sharing module 136, the patient's combined respiratory therapy prescription has been electronically sent to the home care company's computer. As a result, the company knows which combination device 110 it needs to provide for the patient and also knows the patient's specific respiratory therapy treatment plan.

Using the data sharing module 136 as implemented on his or her handheld device, a home care therapist employed by the home care company downloads the patient's combined respiratory therapy prescription to his or her handheld device and brings it to the patient's home. The therapist may then use the data sharing module 136 to transfer the patient's combined respiratory therapy prescription directly to the control module 120 of the combination device 110 (e.g., by connecting his or her handheld device to the combination device 110). If a prescription translation module 122 is installed on the therapist's handheld device, the prescription may be translated to machine-readable instructions at the hand held device and then implemented directly by the combination device 110. Alternatively, the prescription may be translated by the prescription translation module 122 of the control module 120.

During or after a therapy session, the combination device 110 can send data about the therapy session or data relating to the patient's condition or preferences to the clinician's handheld device (e.g., in the form of a notification message). Based on this notification and, perhaps, a telephone follow-up with the patient, the clinician can use the problem-first module 140 to change the patient's combined respiratory prescription and send the new prescription to the device 110 using the data sharing module 136. Using the data sharing module 136, the new or changed prescription can be made available at a display of the device 110 or at other electronic devices, for viewing by the home care company, other caregivers, the patient, and/or family members of the patient, for example.

The audio interface module 142 includes a software-based user interface to the prescription creator module 112, which allows the patient and/or family members or others associated with the patient to view the patient's combined respiratory therapy prescription and configure reminders, alerts, and other messages relating to the patient's therapy prescription. In some embodiments, the audio interface module 142 provides a software-driven, human-voice natural language interface to the combination device 110. The audio interface 142 maps pre-recorded human voice messages (or computer-synthesized spoken natural language messages) to various aspects of the patient's combined respiratory therapy prescription, as may be desired by the patient or configured by a caregiver or family member. For example, the recorded messages may provide instructions on how to use the combination device 110 or adjust its settings. These instructional-type messages may be timed to be played prior to the start of a therapy session or upon the user's request. For example, the patient may input a coded question such as "how do I turn this device on?" and in response, the audio interface 142 may provide the requested instructions.

In some embodiments, the audio interface 142 may be programmed to play recorded messages of an inspirational or reassuring nature at appropriate times, prior to, during, or after a therapy session. In some cases, the content and timing of these types of messages is based on the patient's preferences, focus groups, and/or research relating to the psychology of people who have chronic illnesses. For example, patients with chronic illnesses may have psychological profiles that could impair their compliance with the use of respiratory therapy devices and other medical devices, such as chronic anxiety or social or behavioral disorders. Additionally, pediatric patients can be especially fearful of mechanical devices. Thus, the use of respiratory care devices and other medical devices can be viewed as a burden rather than a benefit by many patients, resulting in poor compliance and limited device efficacy. The audio interface 142 is therefore designed to implement the concept of anthropomorphism (the attribution of human characteristics to non-living things) to improve patient compliance with his or her combined respiratory therapy prescription by making the device 110 more appealing and enjoyable to use.

The audio interface 142 also allows the patient or other user to choose (e.g., from a list of choices presented on a touchscreen display of the configurable user interface module 114) the timing of the desired messages. For example, the patient may specify that a message is to be played in the morning, on the patient's awakening, before the start of a treatment session, during a treatment session, after a treatment session, and/or at bedtime. In other words, a particular recorded message may be linked to one or more portions of the patient's combined respiratory therapy prescription (e.g., treatment sessions and/or treatment sequences) over the course of a treatment pattern (e.g., a 24-hour timeline).

Figure 5:
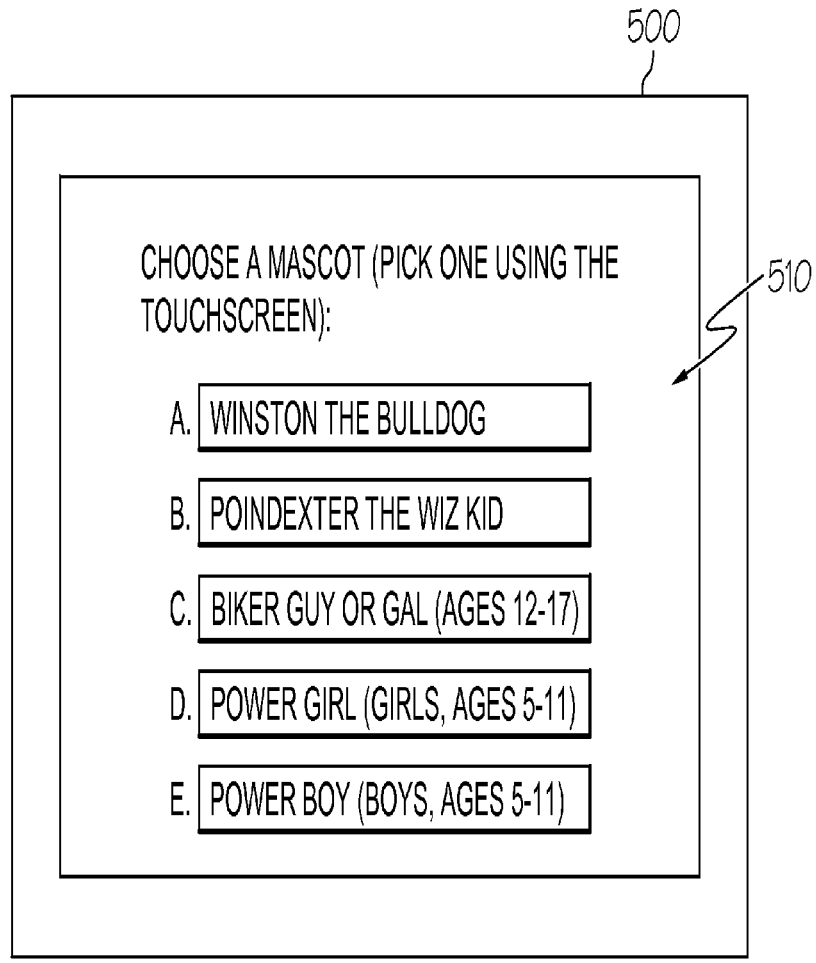
FIG. 5 is a simplified elevational view of at least one embodiment of another user interface for a patient interface module of at least one embodiment of the system of FIG. 1.

In the illustrative embodiments, the audio interface module 142 interfaces with a persona configuration module 144, which allows the patient to select an identity or personality to be ascribed to the combination device 110. An example of a user interface that may be implemented by the configurable user interface module 114 in connection with the persona configuration module 144 is shown in FIG. 5. In FIG. 5, an illustrative display screen 500 includes a number of selectable choices 510, each of which embodies a different persona or "mascot" that may be ascribed to the combination device 110. The selection of a choice 510 automatically configures the character of the voice (e.g., pace, tone) and the content of the pre-recorded audio messages to correspond to the selected persona/mascot. In some embodiments, a graphical or animated depiction of the selected character may be displayed to the user, as well.

The illustrative display screen 500 is a touch-sensitive screen such that selection of a choice 510 can be accomplished by the patient or another user simply touching the desired choice on the screen with a hand, finger, stylus, or the like. Once a choice 510 is selected, the persona configuration module 144 configures the content, timing, voice, and intonation of the pre-recorded audio messages to correspond to the selected persona. To do so, the persona configuration module 144 may select and download recorded messages from a pre-recorded message database that are tagged or otherwise associated with the selected persona. For example, the pre-recorded message database may associate the characteristics of "reliable," "tenacious," and "determined" with the "Winston the Bulldog" persona, and so on. In this way, the combination device 110 can be customized to project a set of human characteristics that appeal to the patient, so that the patient may perceive the device 110 as an ally and companion rather than as an inanimate object that is a threat or a burden, and thereby facilitate interactions between the patient and the combination device 110.

One illustrative example of how the audio interface module 142 and the persona configuration module 144 can be used to customize the message output provided by the combination device 110 is as follows. Suppose a patient would like her combination device 110 to exhibit the human qualities of tenacity and reliability. The patient can use the touchscreen display to input these desired characteristics to the audio interface module 142 (by, for example, selecting them from a drop-down list). The persona configuration module 144 maps the patient's choices to one or more pre-defined personas, which it displays in the list of selectable choices 510 on the display screen 500. From the list of choices 510, the patient selects choice D, "power girl." As a result, the audio interface 142 plays a reassuring message each night, just before the combination device 110 begins a therapy session to assist the patient's breathing during sleep, such as, "I will help you breathe comfortably all night. If you need a cough, just let me know by pressing your thumb switch. I won't let you down. See you in the morning!"

In some embodiments, aspects of the audio interface 142 are adapted for use by clinicians, therapists, or other users, alternatively or in addition to its use in connection with the patient. For example, the audio interface 142 may be configured to output instructions for preparing a combined respiratory therapy prescription or instructions for using the combination device 110, in a spoken natural language form, to a caregiver. As another example, the audio interface 142 may be configured as an interface to the problem-first module 140 of the device control module 140, described above.

Figure 2:
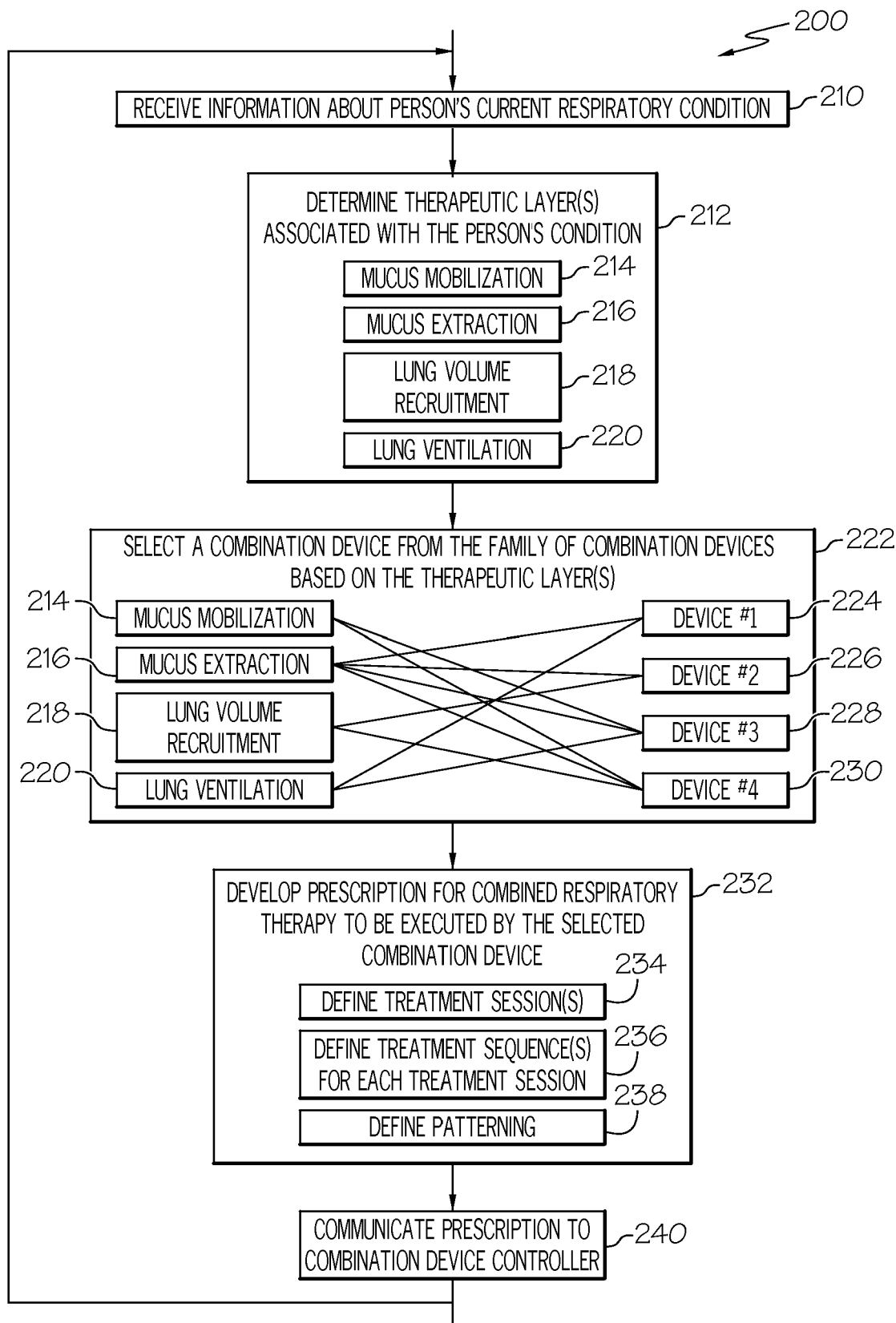
FIG. 2 is a simplified flow diagram of at least one embodiment of a method for configuring a combination respiratory therapy device.

Referring now to FIG. 2, an illustrative method 200 executable as computerized programs, routines, logic and/or instructions by the combined respiratory therapy prescription creator module 112 and/or one or more of the other modules of the system 100 to create a combined respiratory therapy prescription for a patient is shown. The method 200 may be viewed as one example of how the combined respiratory prescription creator module 112 could work. In that case, the primary user would likely be a physician using the method 200 to create a prescription for one of his or her patients. At block 210, the method 200 receives information about a patient's respiratory condition. Such information may include a symptom or a recent change in the patient's clinical condition, which may be input by a clinician, such as a physician, or by a caregiver, or even by the patient or a family member, for example (using, e.g., the problem-first device control module 140). At block 212, the method 200 determines which of the therapeutic layers (e.g., mucus mobilization 214, mucus extraction 216, lung volume recruitment 218, lung ventilation 220) are associated with the information about the patient's condition received at block 210. For example, if the input at block 210 indicates that the patient is having trouble generating a productive cough on his or her own, the method 200 maps that information to one or more of the therapy layers 214, 216, 218, 220 that are directed to providing cough assistance. In this case, those therapy layers include the mucus extraction and either lung ventilation or lung volume recruitment therapy layers. Alternatively, the method 200 may receive information about the patient's respiratory condition, as mentioned above, from the clinician creating the combined respiratory therapy prescription, and the clinician may select and determine the therapeutic layers by himself or herself (e.g., manually), using, for example, the combined respiratory therapy prescription creator module 112.

The determination of whether to select lung ventilation 220 or lung volume recruitment 218 can be based on additional inputs received at one or more of the modules 114, 120, or stored information about the patient's current health condition or clinical history. For example, at block 212, the method 200 may access electronic medical records associated with the patient and thereby determine that the patient has responded well in the past to lung ventilation therapy provided after mucus extraction therapy. As another example, the method 200 may access date and time information that is automatically kept by the system 100, determine therefrom that the patient is likely to be awake and able to participate at the time of the therapy session, and select the lung volume recruitment therapy layer 218, rather than the lung ventilation therapy layer 220, as a result.

Once the therapy layers associated with the patient's condition have been determined, at block 222, the method 200 automatically selects an appropriate combination device 110 from the family of combination respiratory therapy devices, based on the therapy layers determined at block 212. Illustratively, the family of combination devices includes four combination devices 224, 226, 228, 230. The mapping of therapy layers 214, 216, 218, 220 that can be provided by each of the devices 224, 226, 228, 230 is shown illustratively by lines connecting the various therapies with the corresponding combination devices, in block 222. For example, the combination device 224 can be used to provide both mucus extraction and lung ventilation therapies. The combination device 226 can provide both mucus extraction and lung volume recruitment. The combination device 228 can provide all three of mucus mobilization, mucus extraction, and lung ventilation therapies. The combination device 230 can provide all three of mucus mobilization, mucus extraction, and lung volume recruitment therapies. The method 200 determines which of the combination devices 224, 226, 228, 230 to select based on each device's capabilities in relation to the therapy layers 214, 216, 218, 220 determined at block 212 to be needed by the patient. For example, if the patient needs mucus mobilization, the method 200 may select either device 228 or device 230, but not device 224 or device 226. If the patient needs cough assistance therapy but can otherwise breath on his or her own, the method 200 may select device 226 or device 230, but not device 224 or device 228.

Once a combination device has been selected, at block 232, the method 200 obtains the information it needs from the user to prepare a combined respiratory therapy prescription for the patient using the combination device 110 selected at block 222. To do this, the method 200 interfaces with the user to define one or more treatment sessions 234, define one or more treatment sequences 236 for each treatment session, and define the treatment patterning 238 over a period of time during which the patient is to receive respiratory care. In the illustrated examples, a treatment session is made up of a number of treatment sequences that are applied consecutively, e.g., repeated successively a defined number of times, where each treatment sequence includes one or more assisted cough cycles followed substantially immediately by lung ventilation or lung volume recruitment therapy. Thus, the duration of a treatment session can depend on the number of treatment sequences to be provided during the treatment session. So, the process of defining the treatment session or sessions 234 involves the method 200 interfacing with the user to specify, over the respiratory care period or "pattern," the number of treatment sessions to be performed, the start time for each treatment session, and the number of treatment sequences to be performed in each treatment session.

Next, the method 200 interfaces with the user to define the details of each of the treatment sequences 236 to be performed in each of the treatment sessions defined at block 234. To do this, the method 200 interfaces with the user to specify the number of assisted cough cycles in each treatment sequence, the inspiratory and expiratory pressures for each cough cycle (e.g., +25 cm water inspiratory pressure, −30 cm water expiratory pressure), the amount (duration of time) of assisted ventilation to follow the cough cycles (e.g., 2 minutes), and the inspiratory and expiratory pressures for the assisted ventilation therapy (e.g., +15 cm water inspiratory pressure, +4 cm water expiratory pressure).

At block 238, the method 200 may interface with the user to define additional respiratory therapies that may be applied to the patient during the respiratory care period or pattern (e.g., a 24-hour period). For example, the caregiver may wish to schedule one or more mucus mobilization therapies to occur prior to a treatment session, or add an additional daytime or night-time lung ventilation or lung volume recruitment therapy. Accordingly, at block 238, the method 200 interfaces with the user to specify the start times, stop times, and device settings for each of the additional desired therapies. Additionally, at block 232, the method 200 may interface with the user to receive other details relating to the combined respiratory therapy prescription. For example, the user may wish to specify that certain portions of the patient's prescription can be modified by the patient or a family member, while other portions can only be modified by the user or an authorized physician, or that some portions can be modified by the patient or family member with the user or physician's authorization. Once the combined respiratory therapy prescription is complete (to the satisfaction of the user), the method 200 electronically communicates the combined respiratory therapy prescription to the combination device 110 for execution by the device 110. As noted above, this can be done using a wired or wireless data communication method.

One illustrative example of a user interface 400 that may be provided in connection with the process of creating a combined respiratory therapy prescription using the system 100 is shown in FIG. 4. The user interface 400 displays a timeline 410, a legend 412 describing the key abbreviations used in the timeline 410, various details of the respiratory care pattern in their sequential order of occurrence along the timeline 410 (described below), and a simulation feature 440 which allows the user to see an animated simulation 442 (e.g., an animated graphic or video clip) of respiratory therapy as it would be applied to the patient's lungs. To view a simulation, the user may select or highlight one of the therapies or treatment sessions displayed on the timeline 410 and then select the view simulation button. The system 100 then locates and accesses a stored simulation that corresponds to the selected therapy or treatment session (where, for example, such simulations may be indexed or tagged according to their associated therapies or treatment sessions and stored in a database).

The illustrative timeline 410 includes two treatment sessions, TS-1 and TS-2, as well as a mucus mobilization therapy session M-2 and a night-time nasal lung ventilation therapy session NIV. Each of these sessions has an associated start time. For example, the treatment session TS-1 has a start time of 8:00 a.m., the mucus mobilization therapy session has a start time of 7:50 p.m., the treatment session TS-2 has a start time of 8:00 p.m., and the night-time nasal lung ventilation therapy session has a start time of 10:00 pm. The start time and/or end time and duration of each of these sessions can be varied using selectable markers 418, 420, 430, 432, 434, 436, 438. For example, the caregiver may select or "click" on a marker and drag or slide it horizontally to the right or left to change the patient's therapy pattern or schedule. Moving a start-time marker (e.g., markers 418, 438, 430, 434) to the left causes the therapy to have an earlier start time, while moving the start-time marker to the right will cause the therapy to start later in the day. Moving an end-time marker (e.g., markers 420, 430, 432, 436) to the left will decrease the duration of the therapy, while moving the end-time marker to the right will increase the therapy duration. In the illustrated example, the marker 430 is both a start-time marker (for the treatment session TS-2) and an end-time marker (for the mucus mobilization therapy MM). This indicates to the system 100 that the treatment session TS-2 is to begin substantially immediately upon the completion of the mucus mobilization session MM. In this way, dependencies between the various therapies can be created so that their performance can be coordinated automatically.

Each of the therapy sessions (TS-1, MM, TS-2, NIV) can have an expand/contract button (e.g., 422, 426, 428) associated with it. The expand/contract buttons 422, 426, 428 can be selected to show or hide further details about the therapy session, such as the number of treatment sequences, the device settings, etc.). In the illustrated example, the expand/contract button 422 has been selected to show further details of the treatment session TS-1. Those details are displayed in a window 414. The window 414 shows that the treatment session TS-1 is made up of 5 treatment sequences. Each of the treatment sequences (SEQ 1, SEQ 2, SEQ 3, SEQ 4, SEQ 5) has its own start and end markers 444, 448, 450, 452, 454, 456, which the user can slide back and forth horizontally to adjust the duration of the treatment sequence (e.g., to adjust the number of cough cycles in the treatment sequence or the duration of the lung ventilation). The markers 448, 450, 452, 454 act as both start and end markers, thereby making the start time for the beginning of the next treatment sequence (e.g., SEQ 2) dependent on the completion of the previous treatment sequence (e.g., SEQ 1) rather than on a specific clock time. Each of the treatment sequences also has an expand/contract button 424, 458, 460, 462, 464 associated with it. As such, the caregiver can view and/or modify the details of a particular treatment sequence by selecting the corresponding expand/contract button 424, 458, 460, 462, 464. In the illustrated example, the button 424 has been selected to show the details for the treatment sequence SEQ 1. As shown in the window 416, these details include four assisted cough cycles with +25 inspiratory pressure/−30 expiratory pressure followed by two minutes of lung ventilation at +15 inspiratory pressure/+4 expiratory pressure. The details shown in the windows 414, 416 can be hidden by selecting the corresponding expand/contract button (e.g., 422, 424) again. Similarly, the simulation 442 can be hidden by selecting the button 440 a second time. In some embodiments, the window 416 is interactive (e.g., it contains one or more text boxes) so that the details shown therein can be edited directly by the caregiver.

Figure 3:
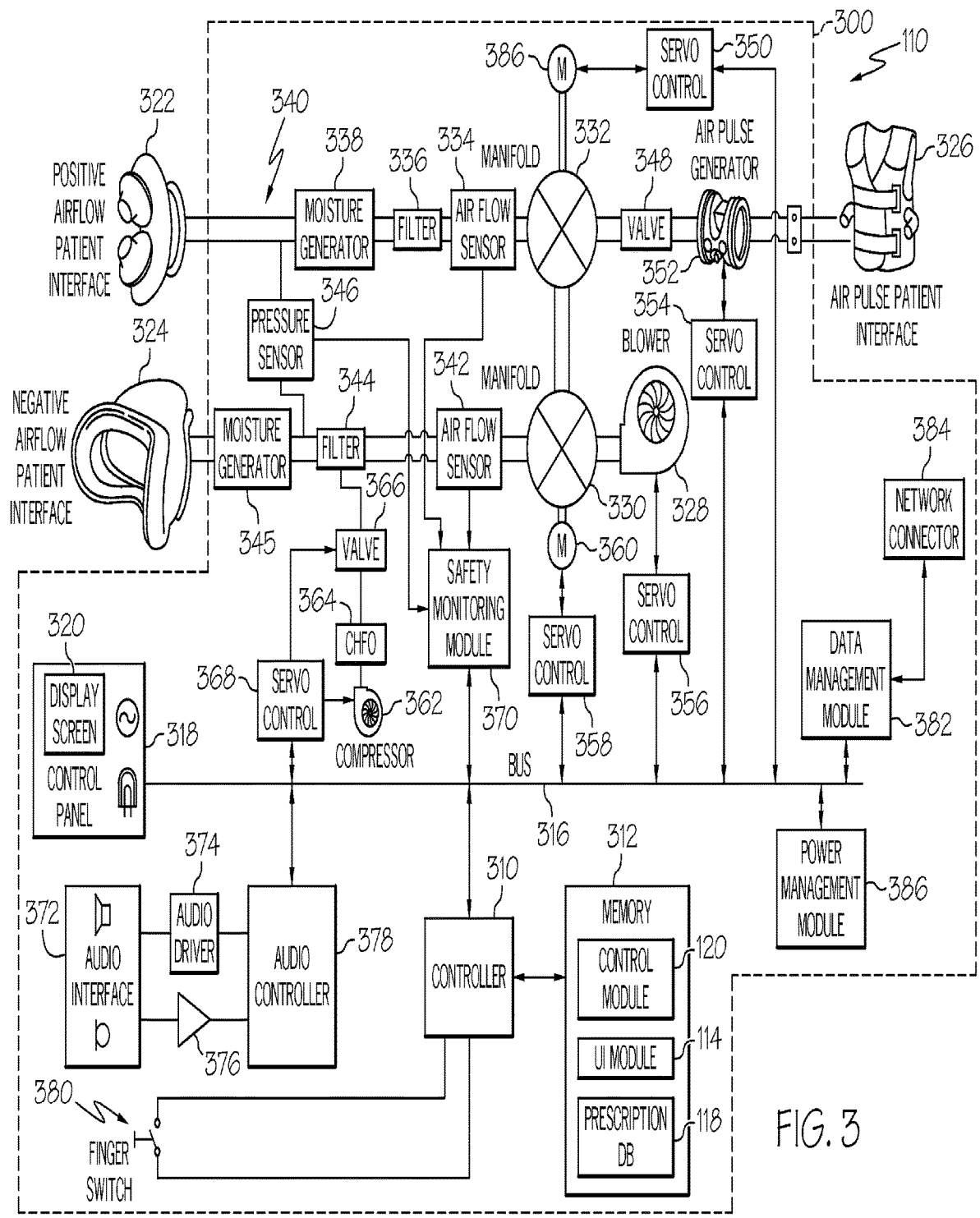
FIG. 3 is a simplified schematic diagram for at least one embodiment of a combination respiratory therapy management system.

Referring now to FIG. 3, an illustrative control unit 300 for the combination device 110 is shown in greater detail. The control unit 300 is embodied as a housing (e.g., plastic or metal), which contains or supports, as the case may be, the electronic and mechanical components shown inside the dashed lines in FIG. 3. In some embodiments, the housing is sized and designed so that the control unit 300 is relatively lightweight and portable. For example, some embodiments of the control unit 300 are configured so that they may be mounted to a patient support apparatus, such as a wheelchair, stretcher, lift, hospital bed, or other patient transport device.

The housing has defined therein a number of ports to which a number of patient interfaces 322, 324, 326 can connect to provide various forms of respiratory therapy to the patient. The positive airflow patient interface 322 is one exemplary embodiment of the positive-pressure airflow patient interface 124 shown in FIG. 1. The patient interface 322 is embodied as a nasally mounted device that contains a pair of air delivery conduits, each of which is configured to engage one of the patient's nostrils. As such, the patient interface 322 is configured to supply positive-pressure airflow to the patient via the patient's nose.

The patient interface 324 is one exemplary embodiment of the negative airflow patient interface 126 of FIG. 1. The patient interface 324 is embodied as mask that is designed to engage with the patient's mouth area to supply airflow through the patient's mouth. In the embodiment of FIG. 3, the patient interface 322 is configured to supply only positive airflow and the patient interface 324 is configured to supply only negative-pressure airflow to the patient. In other words, the illustrative patient interface 324 is only used for the negative-pressure portions of assisted cough cycles, and is not used to provide lung ventilation or lung volume recruitment therapy. Similarly, the patient interface 322 is only used for lung ventilation, lung volume recruitment, and the inspiratory pressure portion of assisted cough cycles, and is not used during the negative-pressure portions of the assisted cough cycles. This configuration of the interfaces 322, 324 keeps the positive and negative air flow circuits separate, and thus free of contamination. In other embodiments, however, the interfaces 322, 324 may be combined or integrated as a single patient interface; for example, as a single patient interface having separate positive and negative airflow circuits.

The air pulse patient interface 326 is one exemplary embodiment of the patient interface 128 shown in FIG. 1. In some embodiments, the interface 326 is embodied as a wearable element to which tubing can be connected to supply air pulses to the patient's chest region when worn. One example of such a device is THE VEST, available from the Hill-Rom Company, Inc. Alternatively or in addition, some embodiments may provide certain forms of air pulse therapy using the negative airflow patient interface 324. For example, a METANEB device or other type of continuous high frequency oscillation (CHFO) device 364 may be connected to the negative airflow patient interface 324. Other devices that provide various forms of air pulse therapy may also be used in a similar fashion.

In the embodiment of FIG. 3, all of the computer programs and other components that provide the functionality of the system 100 reside in the control unit 300. That is, all of the various features of the system 100 provided by the various modules described above can be accessed and used directly at the control unit 300. Accordingly, the illustrative control unit 300 includes therein a controller 310, which may be embodied as one or more microprocessors, microcontrollers, digital signal processors, or the like. The controller 310 communicates electronically with many other elements of the control unit 300 via a data communication link or bus 316 (e.g., a Controller Area Network bus or the like). In some embodiments, the control module 120, the configurable user interface module 114, the prescription database 118, and/or any of their respective submodules, described above, are embodied as software that is stored in e.g., disk storage, and then loaded into memory 312 (e.g., random-access memory (RAM)) at runtime as needed. In some embodiments, portions of the data 118 and/or the modules 114, 120 may be embodied as firmware residing in non-volatile memory. Further, in some embodiments, the memory 312 may be integrated with the controller 310. Accordingly, the simplified illustration of FIG. 3 showing the configurable user interface module 114, the prescription database 118, and the control module 120 embodied in the memory 312, which is accessible to the controller 310, is intended to cover all of the various possible embodiments of the database 118 and modules 114, 120, whether implemented as software, firmware, hardware or a combination thereof.

The control unit 300 includes a control panel 318, which, as indicated by the schematic of FIG. 3, may have its own power supply. The illustrative control panel 318 includes a display screen 320, which may be embodied as a touchscreen display supported by the housing of the control unit 300. During operation, information about the combination device 110, such as the current device settings, as well as therapy being performed, may be displayed on the display screen 320. Features provided by the modules 114, 120, and/or data accessed from the database 118, may be made available through the control panel 318 and/or the display screen 320, or may be provided at other computing devices as described above. In other words, any of the features of the system 100 described above may be accessible to users via the control panel 318 and/or the display screen 320, or through other computing devices as described herein, in various embodiments of the system 100.

The control unit 300 includes an audio circuit illustratively made up of an audio interface 372, an audio driver 374, an amplifier 376 and an audio controller 378. The audio circuit is configured to allow the system 100 to process audio inputs and output audio through speakers as auditory sound, in order to implement the features of the audio interface 142 described above. While the embodiment of FIG. 3 shows the audio circuit as being part of the control unit 300, it should be understood that portions of the audio interface 142 may be implemented at a computing device (such as a user's local computing device) using similar components. As such, the patient or another user may interact with the combination device 110 either via the control panel 318 or via another computing device, in various embodiments of the system 100.

The control unit 300 includes a data management module 382, a network connector 384, and a power management module 386. The data management module 382 manages the communication of data (e.g., portions of the patient's combined respiratory prescription, data generated by the device 110 during operation, etc.) from the device 110 to other devices and vice versa, using the network connector 384. The power management module 382 interfaces with a power supply (e.g., a battery or a wall socket) to supply electrical power to the various components of the control unit 300. The network connector 384 may include a wireless network interface, Ethernet adapter, and/or other components as may be needed or desired to enable the control unit 300 to electronically communicate with other devices through either a wired or wireless network connection.

A finger switch 380 is also provided at the control unit 300 and is in electronic communication with the controller 310. Portions of the finger switch (e.g., a lever, dial, button or toggle) are mounted to the housing of the control unit 300 to be easily accessible to the patient. The controller 310 is configured to turn the execution of the patient's combined respiratory therapy prescription on or off in response to signals received from the finger switch 380. For instance, in some embodiments, the controller 310 is responsive to the finger switch 380 to activate or deactivate an assisted cough therapy. That is, if the patient feels congested and needs to cough, the patient may activate the finger switch to initiate an assisted cough therapy. Similarly, if a therapy is in progress and the patient becomes uncomfortable, the patient may press the finger switch to discontinue or temporarily stop the therapy.

The remaining components of the control unit 300 shown in FIG. 3 include mechanical and electromechanical components to effectuate the various aspects of the patient's combined respiratory therapy prescription through the patient interface(s) 322, 324, 326. In operation, the controller 310 executes the combined respiratory therapy prescription by sending control signals to the various components at the appropriate times, via the bus 316 and a number of servo control modules 350, 354, 356, 358, 368. The servo control modules 350, 358 operate control circuits to control motors 386, 360, respectively, which operate manifolds 332, 330, respectively, to control the flow of air generated by an air supply 328 (e.g., a blower) to the patient interfaces 322, 324, 326. The servo control module 354 operates a control circuit to control the generation of air pulses by the air pulse generator 352 based on airflow received from the air supply 328 through the manifolds 330, 332 and the valve 348. The servo control module 356 controls the operation of the air supply 328 based on parameters supplied by the controller 310 (e.g., on/off, positive/negative airflow, air pressure) in accordance with the combined respiratory therapy prescription. The servo control module 368 operates a control circuit to control the operation of a air supply 362 (e.g., a compressor), which, in some embodiments, may provide airway clearance therapy such as intrapulmonary percussive ventilator (IPV) through a continuous high-frequency oscillation (CHFO) device 364. valve 366, and moisture generator 345 (e.g., a nebulizer) to the nasal patient interface 322.

The patient interfaces 322, 324 are connected to the air supply 328 via the manifolds 332, 330, respectively. The air circuit 340 for the positive-pressure airflow patient interface 322 also includes an airflow sensor 334, a filter 336, and a moisture generator 338, to ensure that air supplied to the patient via the nose is clean, at the correct pressure vis a vis the combined respiratory therapy prescription, and somewhat moist so as to avoid overdrying the patient's nasal passages. Similarly, the air circuit for the negative-pressure airflow patient interface 324 includes an airflow sensor 342 and a filter 344. The airflow sensors 334, 342 and a pressure sensor 346 sense airflow and air pressure, respectively, in their corresponding circuits and provide airflow and air pressure data to a safety monitoring module 370. The safety monitoring module 370 monitors the air circuits for the occurrence of any malfunctions and to ensure that the respiratory therapy is being provided in accordance with the patient's combined respiratory therapy prescription. In some embodiments, the sensors 334, 342, 346 are used to synchronize the operation of the device 110 (e.g., the timing of the application of positive or negative pressure) with the patient's normal breathing pattern as described above. For example, the sensor 346 may detect initiation of a breath by the patient based on the change in air pressure in the air circuit 340, and initiate the inspiratory phase of a cough cycle, lung volume recruitment therapy, or lung ventilation therapy in response. As noted above, in the illustrated embodiment, the air circuits that supply air to the positive-pressure airflow patient interface 322 and the negative-pressure airflow patient interface 324, including the tubing connecting the interfaces 322, 324 to their respective air manifolds 332, 330, are separated from one another.

FIGS. 6-9 illustrate device control algorithms that can be implemented by the system 100 to change various aspects of the patient's combined respiratory therapy prescription and its execution by the combination device 110, in real time (e.g., while the patient is receiving respiratory care). Using the problem-first module 140, for example, the user (e.g., a clinician, caregiver, patient, or family member, as the case may be) can input information about the patient's current respiratory condition, such as "patient can't cough up secretions." The device control module 140 automatically implements therapy adjustments based on the input according to defined algorithms, and then queries the user to determine whether the adjustments were effective. If the user answers that the adjustment didn't help the patient's condition, the system 100 will proceed to the next step in the algorithm as described below with reference to FIGS. 6-9. If the user responds that the adjustment was effective, the system 100 will continue providing therapy according to the current settings, without making any additional changes.

Figure 6:
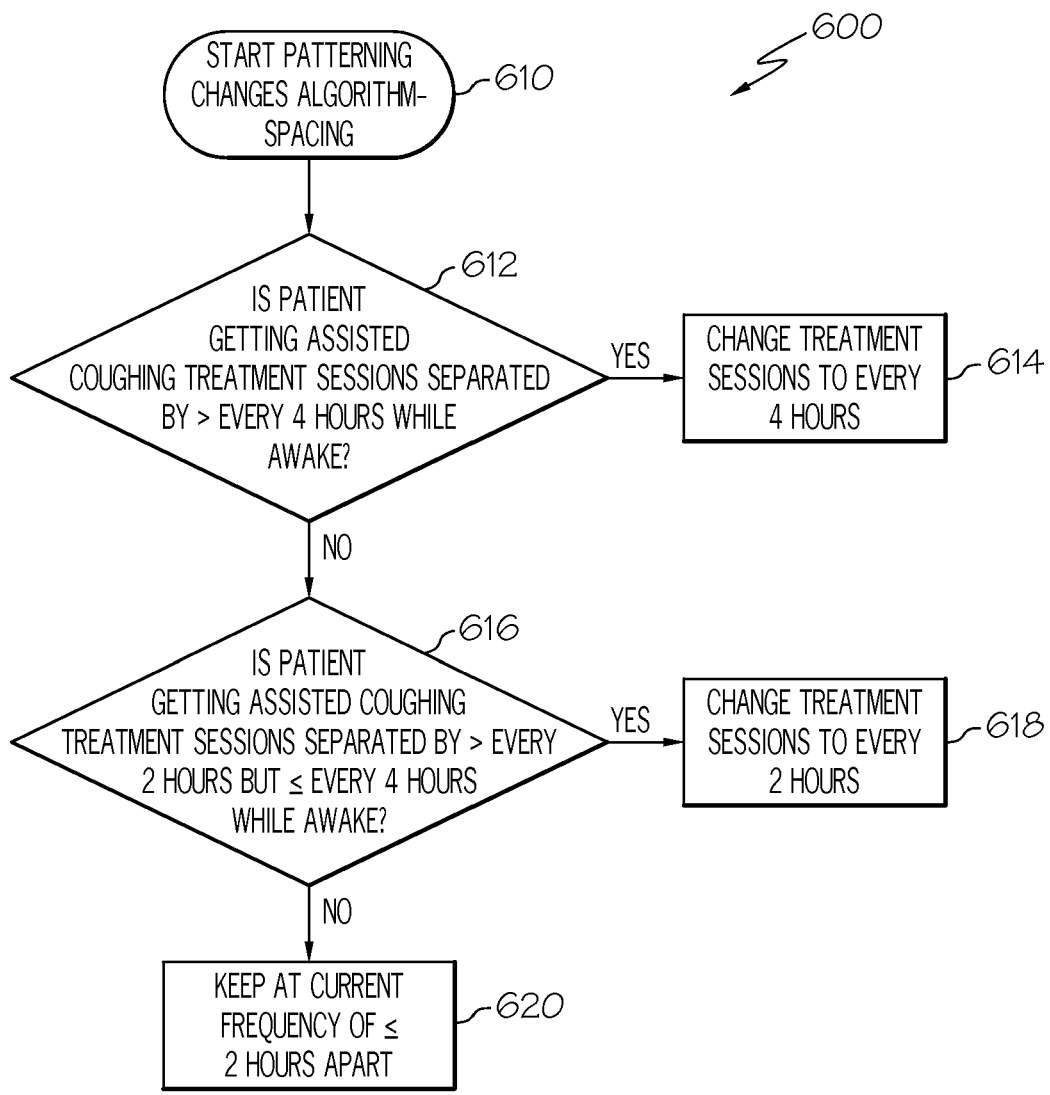
FIG. 6 is a simplified flow diagram of at least one embodiment of a method for configuring respiratory therapy using the system of FIG. 1.

Referring now to FIG. 6, an illustrative method 600 executable as computerized programs, routines, logic and/or instructions by the device control module 140 and/or one or more of the other modules of the system 100 to, in real time, adjust a patterning-spacing aspect of the patient's combined respiratory therapy prescription, either automatically or in response to user input, is shown. In this example, the system 100 detects (either automatically based on sensor data or through analysis of user input) that the "patient can't cough up secretions." The method 600 starts operating at the patterning (e.g., 24-hour timeline) level at block 610, and, at block 612, determines (e.g., automatically or by issuing a query to the user) the spacing of the patient's various therapies over the course of the therapy timeline. For instance, at block 612, the method 600 determines how much time currently elapses between the patient's cough assistance treatment sessions while the patient is awake (e.g., are there more than four hours between each session?). If the answer is yes, the method 600 updates the patient's prescription to change the spacing of the cough assistance treatment sessions during the patient's waking hours to occur every four hours (e.g., to increase the frequency of the treatment sessions), at block 614. If the answer is no that means that the patient is already receiving cough assistance therapy at least every four hours while awake. At block 616, the method 600 determines whether the spacing between treatment sessions is more than two hours but less than or equal to four hours, while the patient is awake. In other words, is the interval between treatment sessions more than two hours but not more than four hours? If the answer is yes, the method 600 updates the patient's combined respiratory therapy prescription so that the cough assistance treatment sessions occur every two hours, at block 618 (e.g., to increase the frequency of the treatment sessions). If the answer is no, then the method 600 maintains the current frequency of cough assistance treatment sessions (deduced as being less than or equal to two hours), at block 620.

Figure 7:
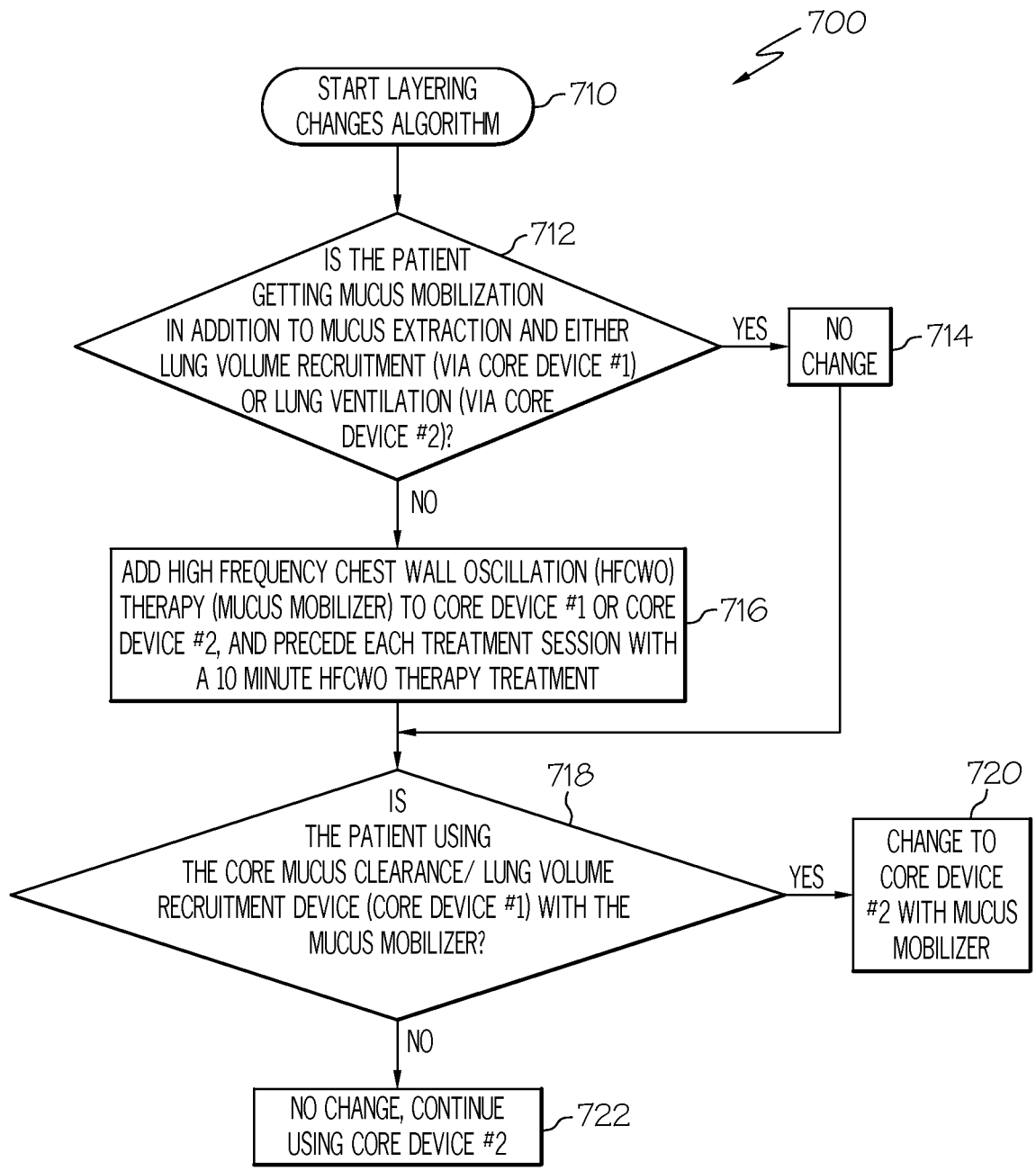
FIG. 7 is a simplified flow diagram of at least one embodiment of another method for configuring respiratory therapy using the system of FIG. 1.

Referring now to FIG. 7, an illustrative method 700 executable as computerized programs, routines, logic and/or instructions by the device control module 140 and/or one or more of the other modules of the system 100 to, in real time, adjust a therapy layering aspect of the patient's combined respiratory therapy prescription, is shown. Whereas the method 600 can be used to adjust the frequency of respiratory treatment sessions over the course of a period of time, the method 700 is directed to determining whether the particular combination device 110 being used by the patient should be changed. At block 710, the layering changes algorithm starts, either automatically or in response to input from a user indicating, for example, a clinical change in the patient's health condition.

At block 712, the method 700 determines (again, either automatically or based on user input) which features of the combination device 110 the patient is presently using, or which combination device 110 from the family of combination devices described above is currently in use. For example, the method 700 may determine whether the patient is already receiving mucus mobilization therapy in addition to mucus extraction therapy and either lung volume recruitment therapy (via the combination device 224, for example) or lung ventilation (via the combination device 226, for example). If the answer is yes, then the method 700 continues providing the current therapy without any changes, at block 714. If the answer is no, then at block 716 the method 700 automatically adds mucus mobilization therapy to the patient's combined respiratory therapy prescription, or instructs the user to do so. This may be accomplished by, for example, activating the air pulse patient interface 128 of the patient's existing combination device 110 or switching the patient to a different combination device (e.g. device 228 or device 230).

Further at block 716, the method 700 updates the patient's combined respiratory therapy prescription to add a ten-minute mucus mobilization therapy session before each scheduled cough assistance treatment session. At block 718, the method 700 determines if the patient is already receiving mucus mobilization therapy using a combination device 110 that is also providing lung volume recruitment therapy to the patient (e.g., device 230). If the patient is already receiving mucus mobilization therapy with lung volume recruitment therapy, then the method 700 displays a message suggesting that the user switch the patient to a device 110 that can provide lung ventilation therapy (in place of the lung volume recruitment therapy) as well as the mucus mobilization therapy (e.g., device 228), at block 720. If the answer is no (meaning that the patient is already receiving both mucus mobilization and lung ventilation therapy), then at block 722 the method 700 displays a message suggesting that the patient continue using the same device 110 without any changes.

Figure 8:
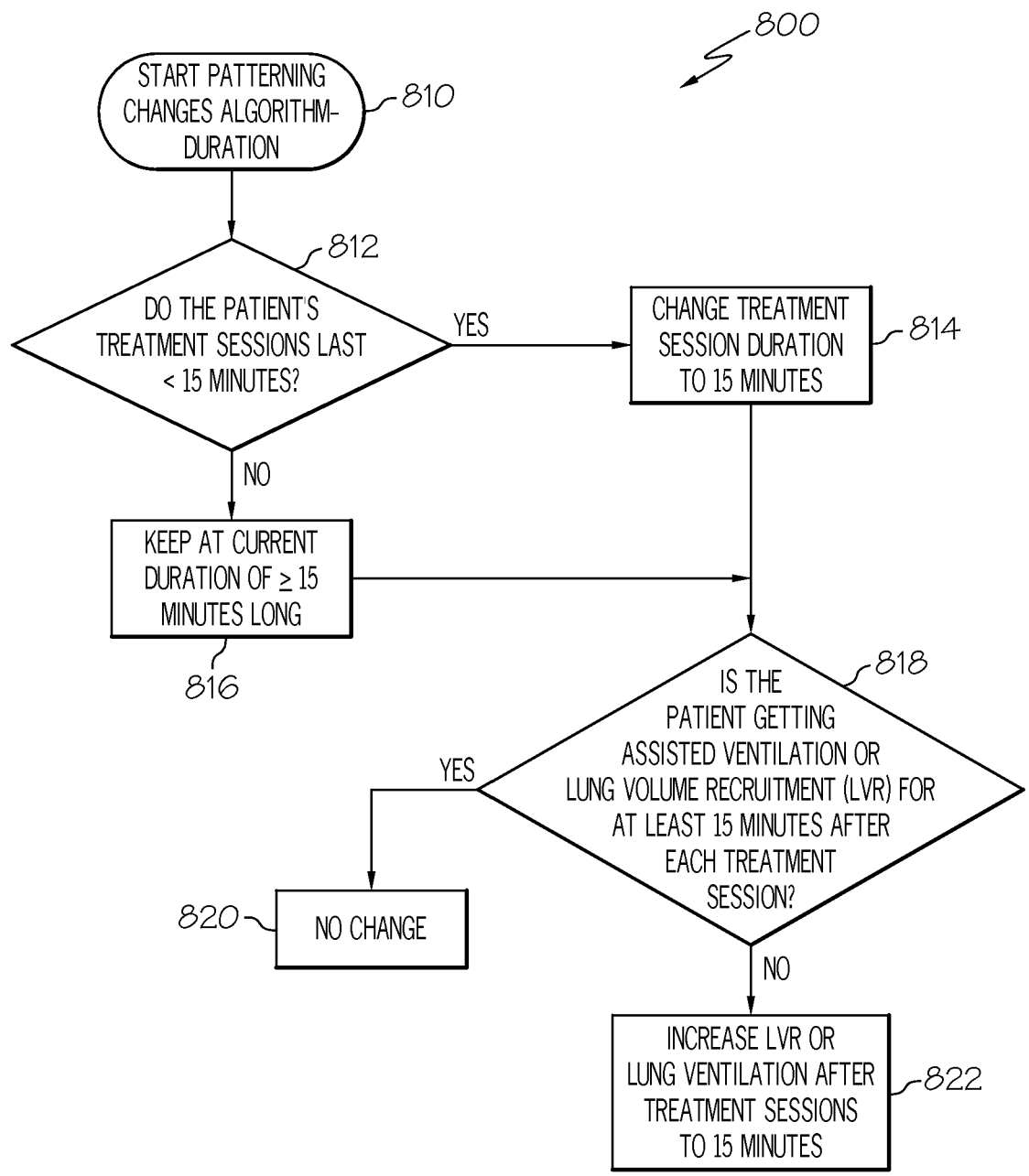
FIG. 8 is a simplified flow diagram of at least one embodiment of another method for configuring respiratory therapy using the system of FIG. 1.

Referring now to FIG. 8, an illustrative method 800 executable as computerized programs, routines, logic and/or instructions by the device control module 140 and/or one or more of the other modules of the system 100 to, in real time, adjust a patterning-duration aspect of the patient's combined respiratory therapy prescription, is shown. Whereas the method 600 may be used to adjust the spacing or time interval between treatment sessions over the course of a respiratory care period (e.g., timeline), the method 800 can be used to, automatically or in response to user input, adjust the length or duration of individual treatment sessions in the patient's prescription. At block 810, the patterning duration change algorithm begins, in response to the system 100 determining, for example, a clinical change in the patient's condition. At block 812, the method 800 determines whether the treatment sessions currently defined in the patient's combined respiratory therapy prescription are shorter in duration than fifteen minutes. If so, the method 700 adjusts the patient's combined respiratory therapy prescription to increase the duration of the treatment sessions to fifteen minutes, at block 814. If not, the method 700 does not make any changes to the existing specifications for the duration of the patient's treatment sessions, leaving them at the current duration of fifteen minutes or longer. At block 818, the method 800 determines whether the patient is receiving either lung ventilation or lung volume recruitment therapy after each treatment session for at least fifteen minutes. If so, the method 800 maintains the current settings for lung ventilation or lung volume recruitment, as the case may be. If not, the method 700 adjusts the patient's combined respiratory therapy prescription to increase the duration of the patient's lung ventilation or lung volume recruitment therapy to fifteen minutes.

Figure 9:
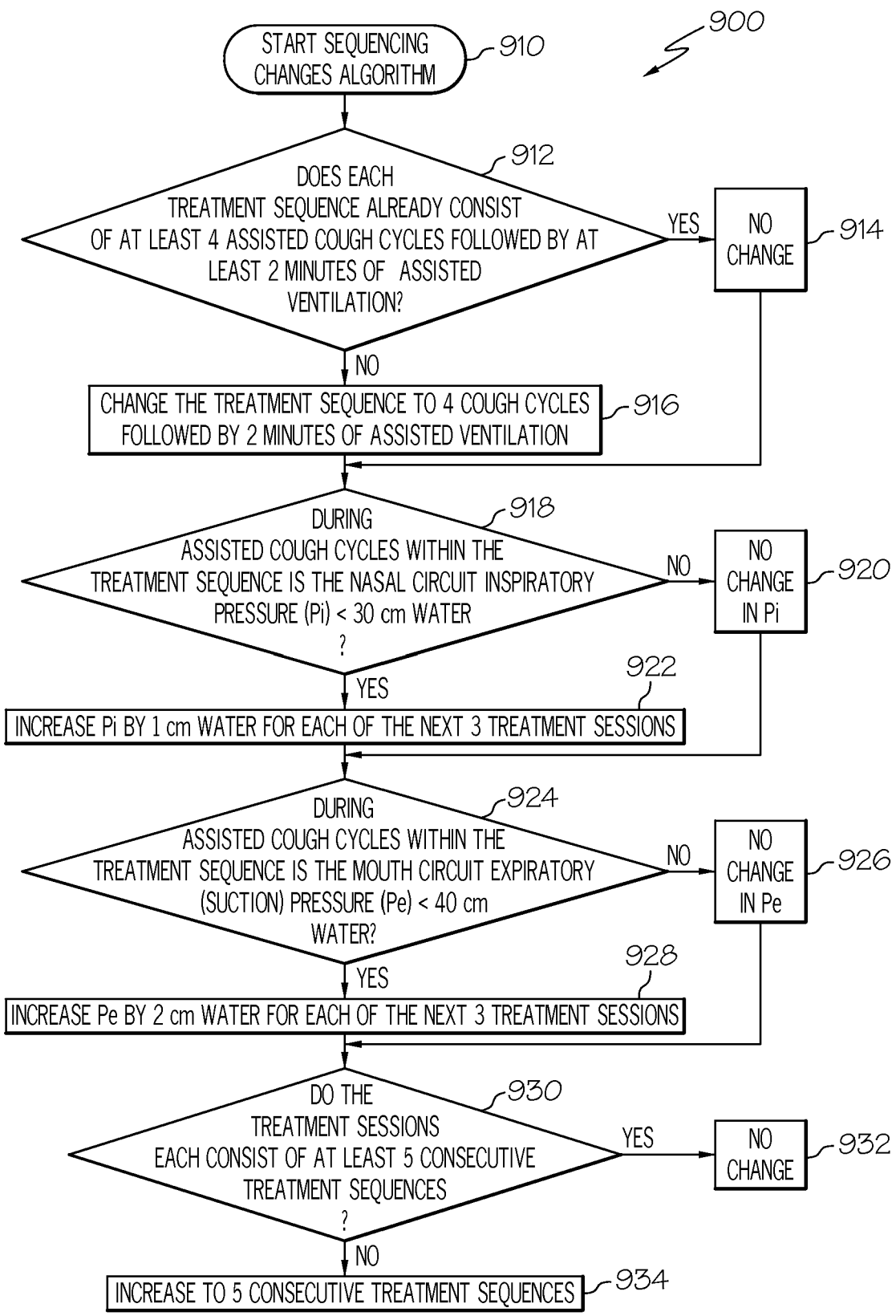
FIG. 9 is a simplified flow diagram of at least one embodiment of another method for configuring respiratory therapy using the system of FIG. 1.

Referring now to FIG. 9, an illustrative method 900 executable as computerized programs, routines, logic and/or instructions by the device control module 140 and/or one or more of the other modules of the system 100 to, in real time, adjust a sequencing aspect of the patient's combined respiratory therapy prescription, is shown. That is, the method 900 is directed to adjusting specific details of cough assistance treatment sequences in response to, for example, clinical changes in the patient's condition, which the system 100 may detect automatically or receive via user input. The method 900 begins at block 910, in response to determining that the patient is having difficulty clearing chest secretions on his or her own. At block 912, the method 900 determines whether the treatment sequences in the patient's current combined respiratory therapy prescription already include four assisted cough cycles followed by at least two minutes of assisted ventilation. If yes, then at block 914 the method 900 continues the therapy according to the existing prescription without making any changes. If no, then at block 916 the method 900 adjusts the patient's existing respiratory prescription to include four cough cycles followed by two minutes of assisted ventilation.

At block 918, the method 900 determines whether the inspiratory pressure used in the cough cycle is less than 30 centimeters (cm) water (e.g., delivered via the nasal patient interface 322). If no (meaning that the inspiratory pressure is already at least 30 cm water), then the method 900 continues the therapy according to the existing prescription without making any changes, at block 920. If yes, the method 900 increases the inspiratory pressure by 1 cm water for each of the next three treatment sessions (e.g., to a maximum of 33 cm water), at block 922. At block 924, the method 900 checks to see if the expiratory pressure (in this case, to the mouth) during the assisted cough cycles is less than −40 cm water (suction). If not (meaning the expiratory pressure is already at least −40 cm water), the method 900 continues the therapy according to the existing prescription without making any changes, at block 926. If yes, the method 900 updates the patient's prescription to increase the expiratory pressure by two cm water for each of the next three treatment sessions (e.g., to a maximum of −46 cm water). At block 930, the method 900 determines whether the patient's treatment sessions are currently defined to include at least five treatment sequences. If yes, the method 900 continues the therapy according to the existing prescription without making any changes. If no, the method 900 updates the patient's prescription to increase the number of consecutive treatment sequences in each treatment session to five.

Figure 10:
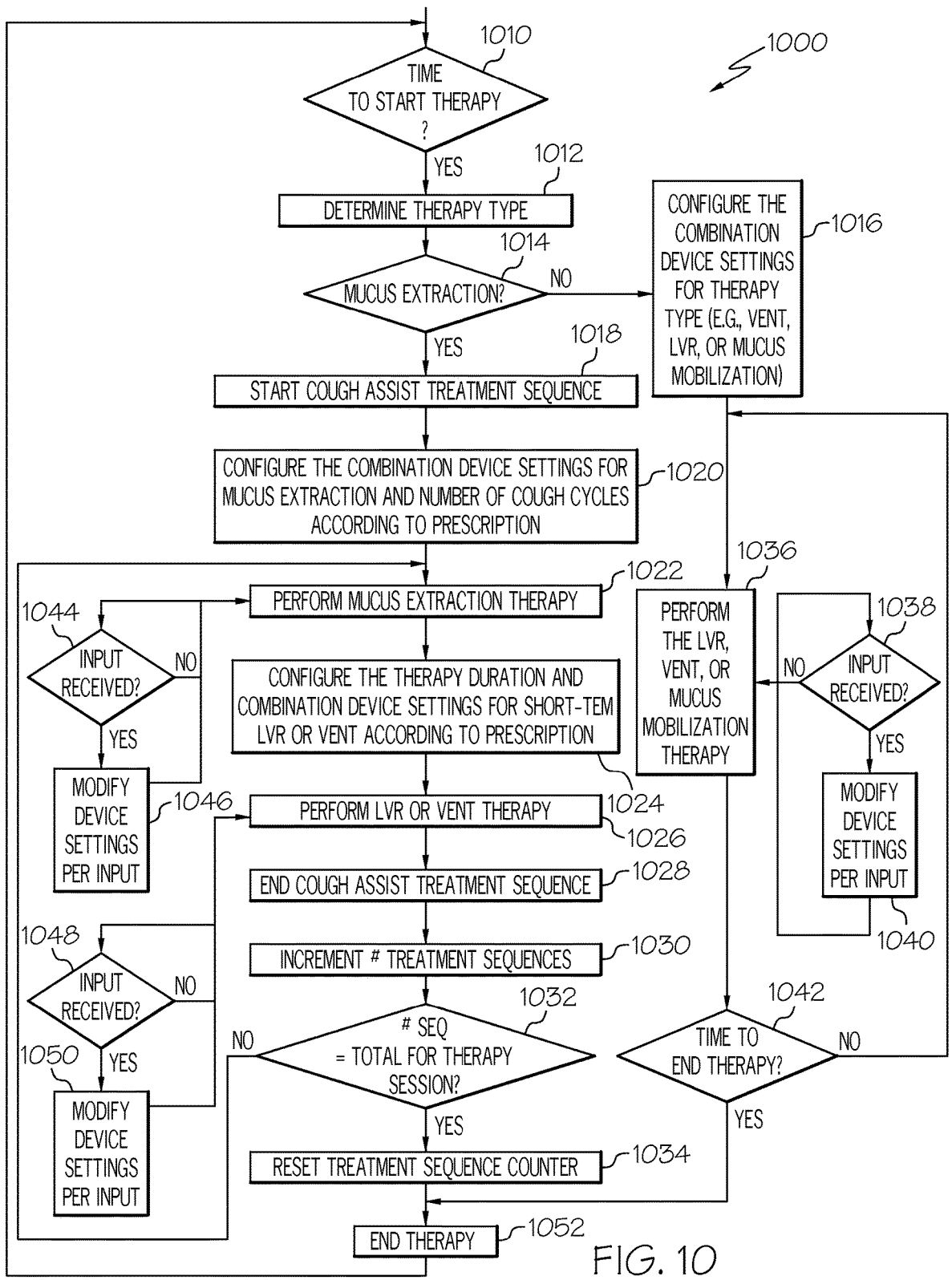
FIG. 10 is a simplified flow diagram of at least one embodiment of a method for performing respiratory therapy using the system of FIG. 1.

Referring now to FIG. 10, an illustrative method 1000 executable as computerized programs, routines, logic and/or instructions by the control module 120 and/or one or more of the other modules of the system 100 to, in real time, operate the combination device 110 to provide the appropriate respiratory therapy to the patient at the appropriate times, is shown. At block 1010, the method 1000 monitors the clock time to determine whether to start a portion of the patient's therapy, according to the patient's combined respiratory therapy prescription. For example, if the patient's prescription indicates that a treatment session is to begin at 8:00 a.m., the method 1000 compares the current clock time to the start time, 8:00 a.m., and when the comparison is successful, proceeds to block 1012. If no therapy is scheduled to begin at the current clock time, according to the patient's prescription, then the method 1000 simply continues to monitor the clock time at block 1010.

At block 1012, the method 1000 determines the type of therapy that it needs to initiate using the combination device 110. If the therapy type is mucus extraction, then at blocks 1014 and 1018, the method 1000 initiates a treatment sequence, which illustratively includes a number of consecutively executed cough cycles. If the therapy type is something other than mucus extraction, then the method 1000 initiates the provision of therapy at block 1016 by configuring the settings of the combination device 110 for the therapy in accordance with the patient's prescription (e.g., therapy pressures, duration, etc.), and performs the therapy at block 1036, for the prescribed period of time. While the therapy is in progress, at block 1036, the system 100 may receive inputs from the user (e.g., a clinician, a caregiver, the patient, or a family member), at block 1038 and adjust the device settings according to the input, at block 1040. For example, the patient may wish to reduce the inspiratory or expiratory pressure and signal the device 110 to do so using the finger switch 380 described above. The method 1000 monitors the time elapsed during the performance of the therapy at block 1036, and at block 1042 determines whether it is time for the therapy to conclude (based on the therapy duration specified in the patient's respiratory prescription). If the requisite amount of time has elapsed, the method proceeds to block 1052 and ends the therapy session. If not, the method returns to block 1036 and continues the current therapy.

Returning to block 1014, the difference between the treatment sequences and other types of therapy is that the duration of a treatment sequence is based at least in part on the number of repetitions of the prescribed cough cycle, rather than on clock time. Thus, for treatment sequences, the method 1000 keeps track of the number of treatment sequences that have already been performed in the current treatment session. So, at block 1018, the treatment sequence counter is initially set to zero. Once a treatment sequence is initiated at block 1018, the method proceeds to configure the combination device 110 for the mucus extraction therapy and for the number of cough cycles specified in the patient's prescription, at block 1020. At block 1022, the method 1000 begins performing the mucus extraction therapy (e.g., by providing the number of cough cycles specified in the prescription). As the treatment sequence specifies that the cough cycles are followed substantially immediately by a short period of either lung volume recruitment or lung ventilation therapy, the method 1000 configures the combination device 110 to provide the lung volume recruitment therapy or lung ventilation therapy upon the completion of the cough cycle, at block 1024, and performs the lung volume recruitment or lung ventilation therapy, at block 1026. To do so, the method 1000 changes the pressure settings from those used for mucus extraction therapy to those that are appropriate for lung volume recruitment or lung ventilation therapy.

Upon completion of the lung volume recruitment therapy or lung ventilation therapy (e.g., upon expiration of the time for providing that therapy, or therapy duration), the method 1000 marks the end of a completed cough assistance treatment sequence, at block 1028, and increments the number of treatment sequences, at block 1030. At block 1032, the method 1000 compares the current number of treatment sequences (e.g., the treatment sequence counter value) to the total number of treatment sequences to be performed during the therapy session, as specified in the patient's combined respiratory therapy prescription. If the value of the treatment sequence counter equals the total number of treatment sequences to be performed during the therapy session, then the therapy session had been completed and the method 1000 proceeds to block 1034 where it resets the treatment sequence counter to zero, and then ends the therapy session, at block 1052. If the value of the treatment sequence counter is less than the total number to be performed during the therapy session, then the method returns to block 1022 to perform another treatment sequence. As with the other forms of therapy, the treatment sequences may be interrupted and modified by user input in real time. This is illustrated by the loops 1044, 1046 and 1048, 1050, each of which operates in a similar manner to the loop 1038, 1040 described above. As such, the description will not be repeated here. At block 1052, the method 1000 returns back to the beginning, block 1010, to continue monitoring the clock time for the start of the next therapy that is to occur according to the patient's combined respiratory therapy prescription.

In the foregoing description of the methods 600, 700, 800, 900, and 1000, references may be made to the method or the system 100 "determining," "checking," "asking the user," etc. It should be understood that whenever a method or another aspect of the system 100 is executing computer logic, the required inputs may be received from a user, calculated automatically, or accessed from a storage location in computer memory. For example, if an illustrative method described herein indicates that the method asks the user for input, it should be understood that other embodiments may not require such user input, and instead may obtain the needed information from, for example, calculations or by accessing a stored database or lookup table. Likewise, illustrative methods described herein as "determining" certain things may do so by obtaining user input, accessing stored information, or performing calculations, as needed. Further, in the illustrative methods 600, 700, 800, 900, and 1000, and in other examples described herein, specific values are mentioned (e.g., air pressures, time durations, etc.). It should be understood that such values are provided for illustration purposes only, and that this disclosure is not limited thereby.

Figure 11:
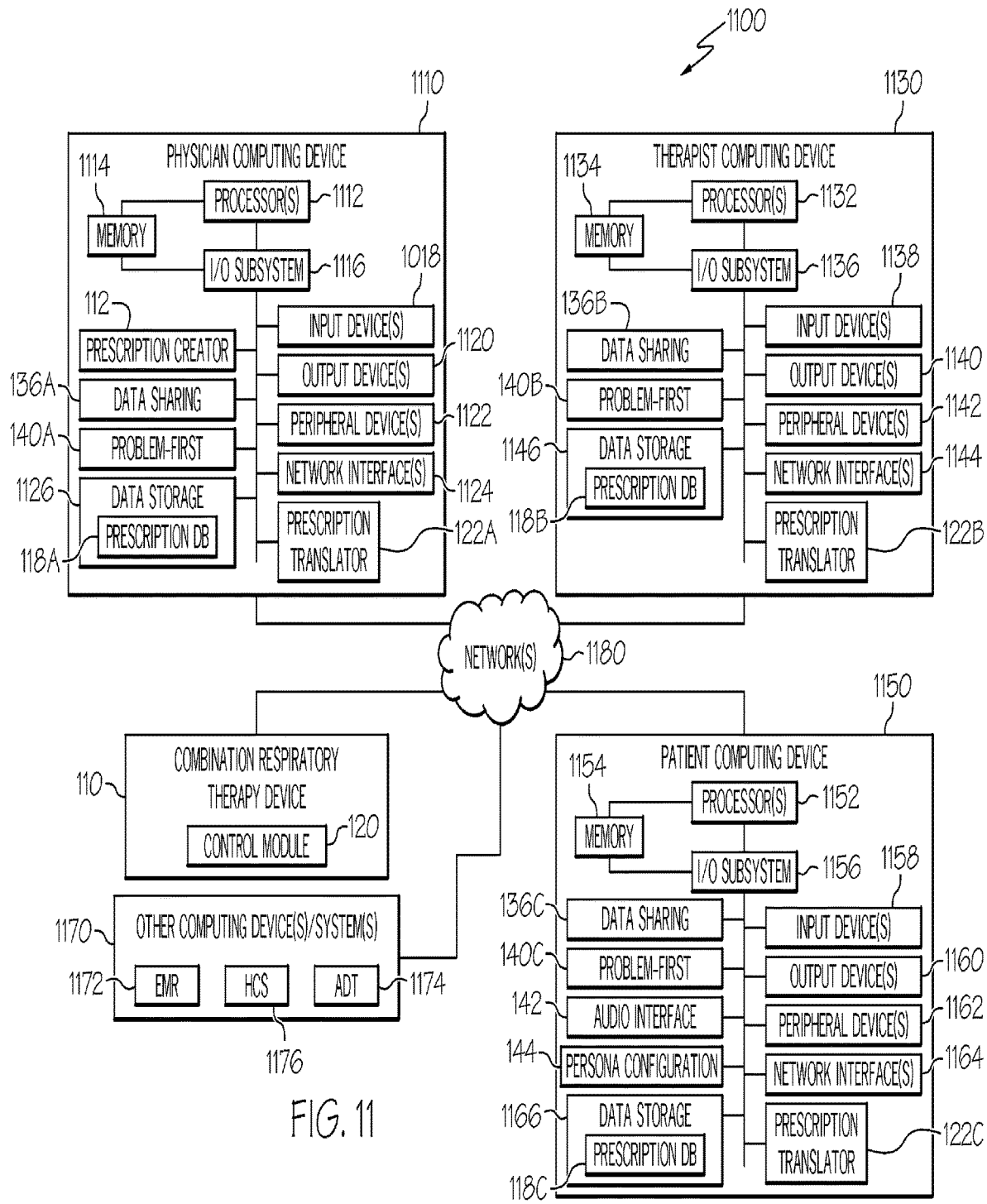
FIG. 11 is a simplified block diagram of an exemplary computing environment in connection with which the system of FIG. 1 may be implemented.

Referring now to FIG. 11, an exemplary computing environment 1100 in which the system 100 may be implemented is shown. Whereas FIG. 3 illustrates an embodiment in which all of the features of the system 100 may be accessible directly at the combination device 110, FIG. 11 illustrates an embodiment in which some of the features of the system 100 may be provided on other devices. Even so, while the computing environment 1100 is shown as involving multiple components and devices, it should be understood that in some embodiments, the computing environment 1100 may constitute a single computing device (e.g., a hospital computer, or a mobile computing device) in combination with the device 110 and/or other devices. In other words, as used herein, the terms "system" and "environment" may refer to a single computing device or a combination of computing devices and/or other components.

The illustrative computing environment 1100 includes a physician computing device 1110, a therapist computing device 1130, a patient computing device 1150, and one or more other computing devices 1170, which are in electronic communication with each other, with other computing devices or systems 1170, and with the combination respiratory therapy device 110, via one or more electronic communication networks and/or telecommunications networks 1180. Each of the devices 1110, 1130, 1150 is configured to use a variation of the system 100 that is appropriate for the type of user. For example, in some embodiments, various permissions and access controls may be selected for each type of user when the system 100 is initially set up or as new users are added.

Illustratively, the prescription creator module 112 resides on the physician computing device 1110, and portions 118A, 118B, 118C of the combined respiratory therapy prescription database 118 are stored on each of the computing devices 1110, 1130, 1150, respectively. The different portions 118A, 118B, 118C of the database 118 may each include subsets of the database 118. For example, the portions 118A and 118B may include the prescriptions for only those patients under the care of the particular physician or therapist using the devices 1110, 1130, and the portion 118C may contain only the prescription for the particular patient using the device 1150. Similarly, portions 136A, 136B, 136C of the data sharing module 136, portions 140A, 140B, 140C of the device control module 140, and portions 122A, 122B, and 122C of the prescription translator module 122 may be configured specifically for the user of the corresponding computing device 1110, 1130, 1150. For example, the data sharing portion 136A and the device control portion 140A may include an extended set of features and capabilities, while the data sharing portions 136B, 136C and the device control portions 140B, 140C may include more limited functionality, based on the intended users of the respective computing devices 1110, 1130, 1150. The prescription translation portions 122A, 122B, 122C may each have the same or similar functionality, or, in some embodiments, the portion 122A may have greater prescription translation capabilities than the portions 1226 or 122C, for example. As shown, the audio interface 142 and the persona configuration module 144 reside on the patient computing device 1150. However, as discussed above, portions or variations of these modules 142, 144 may be adapted for use by other users, such as physicians or therapists, and those portions or alternative versions may reside on one or both of the physician computing device 1110 and the therapist computing device 1130, respectively.

In some embodiments, the computerized modules of the system 100 are embodied as a downloadable software application or "app," which can be obtained from a centralized storage location on a network (such as a private hospital or home care company "app store" or "app market"). In these embodiments, there may be a single app that is downloadable by all types of users, which is then configured for the particular user once installed on the user's local computing device. Alternatively, an app store may provide different downloadable apps for different user types, so that the user may select and download the app that contains the functionality needed by that user. For example, one app may contain the prescription creator module 112 while another app may contain the audio interface and persona configuration modules 142, 144 but not the prescription creator module 112. Of course, permissions and access controls for downloading the apps may be set by an authorized person such as a hospital system administrator.

Each of the illustrative computing devices 1110, 1130, 1150 includes at least one processor 1112, 1132, 1152 (e.g. a microprocessor, microcontroller, digital signal processor, etc.), memory 1114, 1134, 1154, and an input/output (I/O) subsystem 1116, 1136, 1156. The computing devices 1110, 1130, 1150 may be embodied as any type of computing device such as server, an enterprise computer system, a network of computers, a combination of computers and other electronic devices, a personal electronic device such as a mobile, portable, or handheld computing device, smart phone, personal digital assistant, laptop computer, tablet computer, or desktop computer.

Although not specifically shown, it should be understood that the I/O subsystems 1116, 1136, 1156 typically include, among other things, an I/O controller, a memory controller, and one or more I/O ports. The processors 1112, 1132, 1152 and the I/O subsystems 1116, 1136, 1156 are communicatively coupled to the memory 1114, 1134, 1154. The memory 1114, 1134, 1154 may be embodied as any type of suitable computer memory device (e.g., volatile memory such as various forms of random access memory). In the illustrative environment 1100, the I/O subsystems 1116, 1136, 1156 are communicatively coupled to a number of hardware components including various input devices 1018, 1140, 1158 (e.g., a touchscreen, microphone, physical keyboard or keypad, button, or hard panel control), at least one data storage 1126, 1146, 1166, various output devices 1120, 1140, 1160 (e.g., an LED, display screen, speaker), one or more other peripheral devices 1122, 1142, 1162 (e.g., sound, graphics or media adaptors), and one or more network interfaces 1124, 1144, 1164.

The data storage 1126, 1146, 1166 may include one or more hard drives or other suitable data storage devices (e.g., flash memory, memory cards, memory sticks, and/or others). In some embodiments, portions of the prescription database 118A, 118B, 118C reside at least temporarily in the data storage 1126, 1146, 1166. Portions of the prescription database 118A, 118B, 118C may be copied to the memory 1114, 1134, 1154 during operation, for faster processing or other reasons. Further, in some embodiments, portions of any of the software modules of the system 100 may be stored in the data storage 1126, 1146, 1166 and loaded to the memory at runtime.

The network interfaces 1124, 1144, 1164 may communicatively couple the computing devices 1110, 1130, 1150 one or more networks 1180. Such other networks may include a local area network, wide area network, enterprise cloud, and/or the Internet, for example. Accordingly, the network interfaces 1124, 1144, 1164 may include a wired or wireless Ethernet, mobile/cell network, WI-FI, BLUETOOTH, VPN (Virtual Private Network), or NFC (Near Field Communication) device or adapter as may be needed, pursuant to the specifications and/or design of the particular network 1180.

Each of the other computing devices/systems 1170 may be embodied as any suitable type of computing device such as, for example, a server, an enterprise computer system, a network of computers, a combination of computers and other electronic devices, a mobile device, any of the aforementioned types of electronic devices, or other electronic devices. For example, in some embodiments, the other computing devices 1170 may include other computers or computer systems of a hospital or other healthcare facility, which run enterprise-type software applications such as electronic medical records (EMR) systems 1172, admission, discharge, and transfer (ADT) systems 1174, and healthcare communication systems (e.g., nurse call systems) 1176. Thus, in some embodiments, the system 100 may communicate with one or more of the systems 1172, 1174, 1176. For example, if a patient undergoing combined respiratory therapy using the device 110 has a clinical change in his or her health condition that requires medical attention, the system 100 may communicate an alert to the responsible nurse or therapist via the healthcare communication system 1176. As another example, the system 100 may obtain data about the patient's medical history or history of previous treatments from the electronic medical records system 1172 and use that information to configure or adjust the patient's current therapy prescription. Additionally, the system 100 may interface with a healthcare facility's admission, transfer and discharge system 1174 to, for example, automatically send the patient's combined respiratory prescription to a remote computing device upon the patient's discharge from the facility.

The computing environment 1100 may include other components, sub-components, and devices not illustrated in FIG. 11 for clarity of the description. In general, the components of the computing environment 1100 are communicatively coupled as shown in FIG. 11 by signal paths, which may be embodied as any type of wired or wireless signal paths capable of facilitating communication between the respective devices and components.

In the foregoing description, numerous specific details, examples, and scenarios are set forth in order to provide a more thorough understanding of the present disclosure. It will be appreciated, however, that embodiments of the disclosure may be practiced without such specific details. Further, such examples and scenarios are provided for illustration, and are not intended to limit the disclosure in any way. Those of ordinary skill in the art, with the included descriptions, should be able to implement appropriate functionality without undue experimentation.

References in the specification to "an embodiment," etc., indicate that the embodiment described may include a particular feature, structure, or characteristic, but every embodiment may not necessarily include the particular feature, structure, or characteristic. Such phrases are not necessarily referring to the same embodiment. Further, when a particular feature, structure, or characteristic is described in connection with an embodiment, it is believed to be within the knowledge of one skilled in the art to effect such feature, structure, or characteristic in connection with other embodiments whether or not explicitly indicated.

Embodiments in accordance with the disclosure may be implemented in hardware, firmware, software, or any combination thereof. Embodiments may also be implemented as instructions stored using one or more machine-readable media, which may be read and executed by one or more processors. A machine-readable medium may include any mechanism for storing or transmitting information in a form readable by a machine (e.g., a computing device or a "virtual machine" running on one or more computing devices). For example, a machine-readable medium may include any suitable form of volatile or non-volatile memory.

In the drawings, specific arrangements or orderings of schematic elements may be shown for ease of description. However, the specific ordering or arrangement of such elements is not meant to imply that a particular order or sequence of processing, or separation of processes, is required in all embodiments.

In general, schematic elements used to represent instruction blocks or modules may be implemented using any suitable form of machine-readable instruction, and each such instruction may be implemented using any suitable programming language, library, application programming interface (API), and/or other software development tools or frameworks. Similarly, schematic elements used to represent data or information may be implemented using any suitable electronic arrangement or data structure. Further, some connections, relationships or associations between elements may be simplified or not shown in the drawings so as not to obscure the disclosure.

This disclosure is to be considered as exemplary and not restrictive in character, and all changes and modifications that come within the spirit of the disclosure are desired to be protected. For example, while aspects of the present disclosure may be described in connection with particular types and features of respiratory therapy devices, it should be understood that the various aspects are applicable to other types and features of such devices.

The invention claimed is:

1. A combined respiratory therapy system, comprising:
a combination respiratory therapy device comprising a blower for providing negatively pressurized air to a mouthpiece coupled to a patient's airway and an air pulse generator configured for delivering air pulses to at least one of a garment worn by the patient or a nasal interface worn by the patient, wherein the blower and the air pulse generator are resident on physically separate circuits, the combination respiratory therapy device further comprising a network interface in communication with an associated computer network, and a controller including a processor in communication with memory storing instructions which are executable by the processor to execute a combined respiratory therapy prescription, the combined respiratory therapy prescription defining a plurality of different therapy sessions to be performed by the combination respiratory therapy device over a period of time, each of the plurality of different therapy sessions comprising at least a mucus extraction therapy followed substantially immediately by a lung ventilation therapy or a lung volume recruitment therapy;
a physician computing system in communication with the combination respiratory therapy device via the associated computer network, the physician computing system storing a prescription creator module embodied in one or more machine-accessible storage media, wherein the prescription creator module is executed by the physician computing system to interact with a physician to create the combined respiratory therapy prescription and communicate the combined respiratory therapy prescription to the combined respiratory therapy device; and
wherein the controller of the combination respiratory therapy device, responsive to the created combined respiratory therapy prescription, executes the therapy sessions via providing negatively pressurized air to the mouthpiece, and delivering air pulses to at least one of the garment or the nasal interface.

2. The system of claim 1, wherein the physician computing system further comprises a data sharing module embodied in one or more machine-accessible storage media, wherein the data sharing module is executed by the physician computing system to electronically communicate the combined respiratory therapy prescription to the combination respiratory therapy device via the associated computer network.

3. The system of claim 2, wherein the data sharing module is executable by the physician computing system to electronically communicate the combined respiratory therapy prescription to another computing device.

4. The system of claim 2, wherein the data sharing module is executable by the physician computing system to display at least a portion of the combined respiratory therapy prescription at another computing device used by healthcare personnel.

5. The system of claim 2, wherein the data sharing module is executable by the physician computing system to electronically communicate at least a portion of the combined respiratory therapy prescription from a remote computing device used by healthcare personnel to the combination respiratory therapy device.

6. The system of claim 2, wherein the data sharing module is executable by the physician computing system to display at least a portion of the combined respiratory therapy prescription at another computing device used by a person receiving the combined respiratory therapy.

7. The system of claim 2, wherein the data sharing module is executable by the physician computing system to electronically communicate at least a portion of the combined respiratory therapy prescription from a computing device used by a person receiving the combined respiratory therapy to the combination respiratory therapy device.

8. The system of claim 2, wherein the data sharing module is executable by the computing system to enable two-way electronic communication of at least a portion of the combined respiratory therapy prescription between or among a plurality of computing devices used by a plurality of healthcare personnel.

9. The system of claim 2, further comprising a plurality of additional combination respiratory therapy devices, wherein the prescription creator module is further executed by the physician computing system to map a plurality of therapy layers selected by the physician to one or more additional combination respiratory therapy devices from among the plurality thereof.

10. The system of claim 9, wherein the prescription creator module is further executed by the physician computing system to select one of the one or more combination respiratory therapy devices, and define one of the plurality of different therapy sessions of the combined respiratory therapy in accordance with the physician interaction.

11. The system of claim 10, wherein the prescription creator module is further executed by the physician computing system to define a pattern of respiratory care to be applied via the selected combination respiratory therapy device to the patient over a defined period of time.

* * * * *